United States Patent [19]

Takematsu et al.

[11] Patent Number: 4,753,674
[45] Date of Patent: Jun. 28, 1988

[54] HERBICIDAL COMPOSITION CONTAINING A PHENOXYALKYLAMIDE DERIVATIVE AND METHOD FOR CONTROLLING WEEDS BY THE USE OF THE SAME

[75] Inventors: Tetsuo Takematsu; Yasutomo Takeuchi, both of Utsunomiya; Mitsuaki Takenaka, Ube; Seiji Takamura, Ube; Minoru Nishimura, Ube; Tatsuo Okada, Ube; Yasuhisa Fukuda, Ube, all of Japan

[73] Assignee: UBE Industries, Ltd., Ube, Japan

[21] Appl. No.: 579,655

[22] Filed: Feb. 13, 1984

Related U.S. Application Data

[63] Continuation-in-part of Ser. No. 427,284, Sep. 29, 1982, abandoned.

[30] Foreign Application Priority Data

Oct. 20, 1981 [JP] Japan .................. 56-166343
Dec. 28, 1981 [JP] Japan .................. 56-209945
Dec. 28, 1981 [JP] Japan .................. 56-209946
Aug. 10, 1982 [JP] Japan .................. 56-138023
Apr. 5, 1983 [JP] Japan .................. 58-58623

[51] Int. Cl.[4] .............. A01N 37/18; A01N 43/08; A01N 43/10; A01N 43/40
[52] U.S. Cl. .................. 71/118; 71/88; 71/90; 71/94; 546/330; 546/337; 549/76; 549/77; 549/493; 560/314; 564/166; 564/167; 564/168; 564/175
[58] Field of Search ........... 546/330, 337; 549/76, 549/493, 77; 564/166, 167, 168, 178, 175; 260/453; 71/118, 88, 90, 94; 560/314

[56] References Cited

U.S. PATENT DOCUMENTS 3,348,998 10/1967 Spencer et al. ............ 564/175
3,840,596 10/1974 Richter et al. ............ 260/453
3,852,345 12/1974 Richter et al. ............ 260/453
3,865,866 2/1975 Ozaki et al. .............. 549/493
4,007,277 5/1978 Baker et al. .................. 71/88
4,049,424 9/1977 Baker et al. ................ 71/118
4,050,923 9/1977 Baker et al. .............. 564/175
4,051,184 9/1977 Arneklev et al. .......... 564/175
4,067,725 1/1978 Schurter et al. ............. 71/94
4,082,799 4/1978 Baker et al. .............. 564/175
4,082,800 4/1978 Baker et al. ................ 71/118
4,083,867 4/1978 Baker et al. .............. 564/175
4,116,677 9/1978 Walker et al. .............. 71/118
4,119,433 10/1978 Baker et al. .............. 564/175

OTHER PUBLICATIONS

Joshi et al., J. Indian Chem. Soc. vol. 37, No. 11 (1960), pp. 685–686.

Primary Examiner—Catherine L. Mills
Attorney, Agent, or Firm—Frishauf, Holtz, Goodman & Woodward

[57] ABSTRACT

There are disclosed a herbicidal composition containing, as an active ingredient, a phenoxyalkylamide derivative represented by the formula

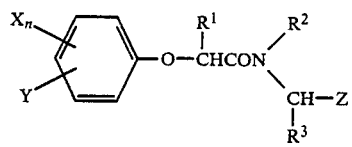

wherein X, n, Y, Z, $R^1$, $R^2$ and $R^3$ have the same meanings as defined in the specification, and a method for controlling weeds by the use of the same. The herbicidal composition according to this invention shows a superior weed-killing activity by pre- and post-emergence treatment in soil.

8 Claims, No Drawings

HERBICIDAL COMPOSITION CONTAINING A PHENOXYALKYLAMIDE DERIVATIVE AND METHOD FOR CONTROLLING WEEDS BY THE USE OF THE SAME

This application is a continuation-in-part of our application Ser. No. 427,284, filed Sept. 29, 1982 now abandoned.

This invention relates to a herbicidal composition containing a phenoxyalkylamide (phenoxyalkanoic acid amide) derivative and a method for controlling weeds by the use of the same as a herbicide. More particularly, this invention relates to a herbicidal composition containing, as an active ingredient, a phenoxyalkylamide derivative represented by the formula (I):

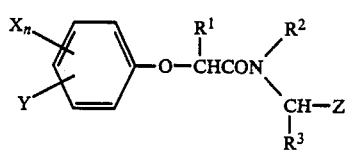

wherein

X: a lower-alkyl group, a lower-alkoxy group, a halogen atom, a cyano group, a nitro group or a propionyl group;

n: an integer of 0 to 3, provided that, when n is an integer of 2 or 3, Xs may be the same or different;

Y: a halogen atom, a lower-alkyl group, a lower-alkoxy group, a trifluoromethyl group or a nitro group;

Z: a phenyl group, a substituted phenyl group represented by the following formula

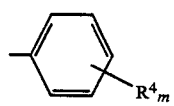

(in which $R^4$ represents a lower-alkyl group, a lower-alkoxy group, a nitro group or a halogen atom; and m is an integer of 1 or 2, provided that, when m is 2, $R^4$s may be the same or different), a naphthyl group, a thienyl group, a pyridyl group, or a furyl group;

$R^1$: an ethyl group or an n-propyl group;

$R^2$: a hydrogen atom, a lower-alkyl group, a lower-alkenyl group, a lower alkynyl group or a lower-alkoxy group; and $R^3$: a hydrogen atom or a lower-alkyl group, and a method for controlling weeds by the use of the same as a herbicide.

In this specification, the term "lower" means to have 1 to 4 carbon atoms. For example, lower-alkyl includes methyl, ethyl, n-propyl, isopropyl, n-butyl, sec-butyl, tert-butyl and the like.

There have long been proposed a large number of herbicidal compositions containing phenoxy series compounds as active ingredients, not a small number of which have been commercially available. Such compounds include, for example, 2,4-D (active ingredient: 2,4-chlorophenoxyacetic acid), 2,4-DP (active ingredient: 2-(2,4-dichlorophenoxy)propionic acid), MCP (active ingredient: 2-methyl-4-chlorophenoxyacetic acid), and MCPCA (active ingredient: N-(2-chlorophenoxy)-2-methyl-4-chlorophenoxyacetamide). In general, these phenoxy series herbicidal compositions known to the art have extremely prominent herbicidal effects against a wide variety of broad leaved weeds as compared with other herbicidal compositions. However, they have common problems that the effect is accompanied by phytotoxicity against rice crops such as tiller depression and induction of monstrosity due to the auxin action.

It is, accordingly, a primary object of this invention to provide a herbicidal composition which comprises as an active ingredient at least one of the phenoxyalkylamide derivative of formula (I) and to provide a herbicidal composition for paddy field which comprises a mixture of the phenoxyalkylamide derivative of formula (I) and 1-(α,α-dimethybenzyl)-3-(4-methylphenyl)urea as active ingredients.

Another object of this invention is to provide a method of use of the above-mentioned phenoxyalkylamide derivative of formula (I) as a herbicide.

The present inventors have synthesized various kinds of phenoxy series compounds and investigated their herbicidal activities. As a result, they have succeeded in synthesizing a group of the phenoxyalkylamide derivative of formula (I), which are not described in the literature, and also found that such new phenoxyalkylamide derivative can show a remarkable herbicidal effect against various weeds generated in a paddy field, a plowed field, an other cultivated and non-cultivated fields, without any phytotoxicity to crops, and have an ability to herbicide weeds selectively. This invention has been, therefore, completed upon these findings.

Representative example of the phenoxyalkylamide derivative (I) is given in Table 1 shown hereinbelow for illustrating purpose only.

In view of the herbicidal effect, preferable is an phenoxyalkylamide derivative represented by the following formula (II):

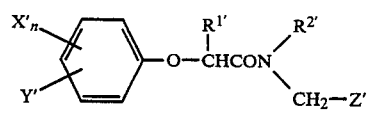

wherein

X': a methyl group or a chlorine atom;

n: an integer of 0 to 3, provided that, when n is an integer of 2 or 3, X's may be the same or different;

Y'; a hydrogen atom or a trifluoromethyl group;

Z': a phenyl group, a 2-methylphenyl group, a 2-chlorophenyl group, a thienyl group, a 2-pyridyl group or a 3-pyridyl group;

$R^{1'}$: an ethyl group; and $R^{2'}$: a hydrogen atom or a methyl group.

As particularly preferable compounds may be mentioned the following compounds.

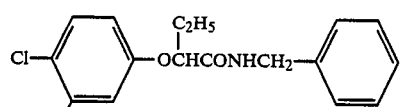

N—Benzyl-2-(4-chloro-3-methylphenoxy)-butyramide

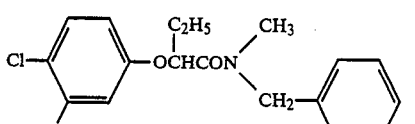

N—Benzyl-N—methyl-2-(4-chloro-3-methylphenoxy)-

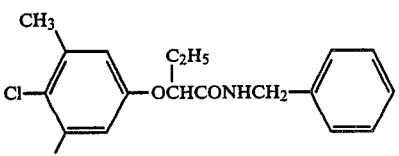
N—Benzyl-2-(4-chloro-3,5-dimethylphenoxy)-butyramide

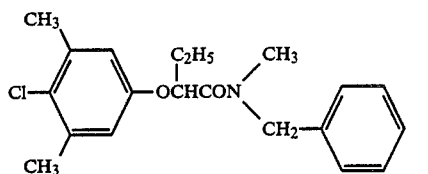
N—Benzyl-N—methyl-2-(4-chloro-3,5-dimethoxyphenoxy)-butyramide

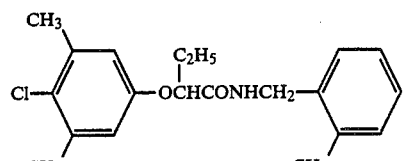
N—(2-Methylbenzyl)-2-(4-chloro-3,5-dimethylphenoxy)-butyramide

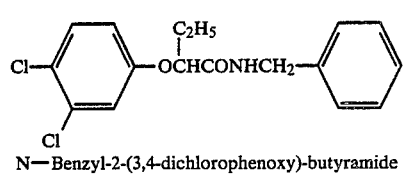
N—Benzyl-2-(3,4-dichlorophenoxy)-butyramide

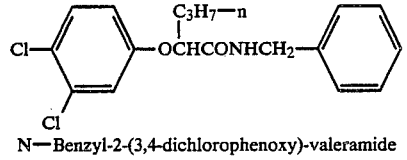
N—Benzyl-2-(3,4-dichlorophenoxy)-valeramide

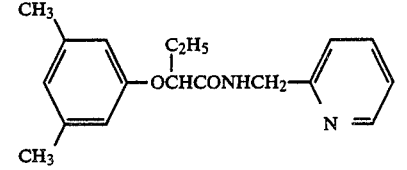
N—(2-Pyridylmethyl)-2-(3,5-dimethylphenoxy)-butyramide

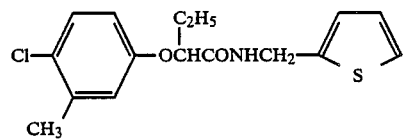
N—Thienylmethyl-2-(4-chloro-3-methylphenoxy)-butyramide

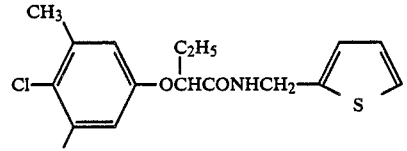
N—Thienylmethyl-2-(4-chloro-3,5-dimethylphenoxy)-butyramide

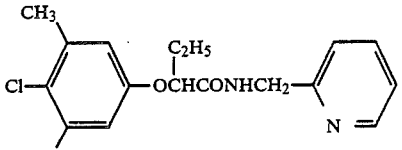
N—(2-Pyridylmethyl)-2-(4-chloro-3,5-dimethylphenoxy)-butyramide

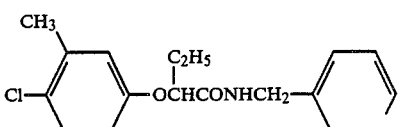
N—(3-Pyridylmethyl)-2-(4-chloro-3,5-dimethylphenoxy)-butyramide

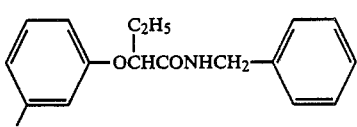
N—Benzyl-2-(3-trifluoromethylphenoxy)-butyramide

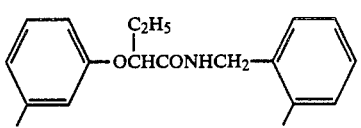
N—(2-Chlorobenzyl)-2-(3-trifluoromethylphenoxy)-butyramide

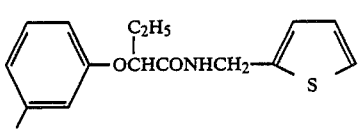
N—Thienylmethyl-2-(3-trifluoromethylphenoxy)-butyramide

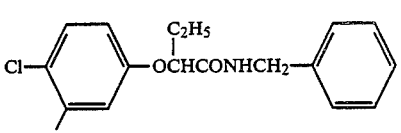
N—Benzyl-2-(4-chloro-3-trifluoromethylphenoxy)-butyramide

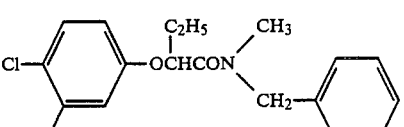
N—Benzyl-N—methyl-2-(4-chloro-3-trifluoromethylphenoxy)-butyramide

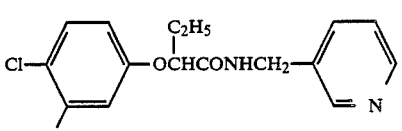
N—(3-Pyridylmethyl)-2-(4-chloro-3-trifluoromethylphenoxy)-butyramide

-continued

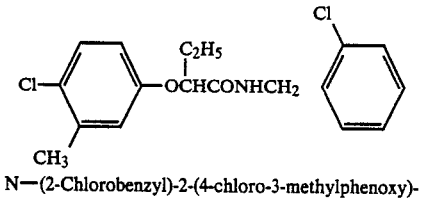
N—(2-Chlorobenzyl)-2-(4-chloro-3-methylphenoxy)-butyramide

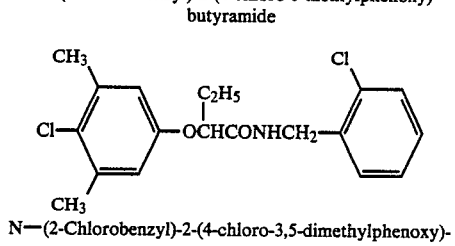
N—(2-Chlorobenzyl)-2-(4-chloro-3,5-dimethylphenoxy)-butyramide

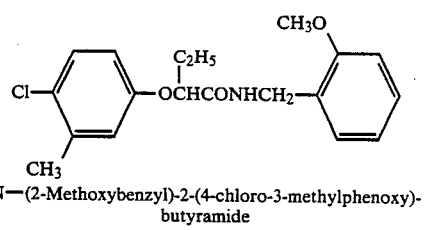
N—(2-Methoxybenzyl)-2-(4-chloro-3-methylphenoxy)-butyramide

In the following Table 1, there will be exemplified phenoxyalkylamide derivatives according to the present invention.

In the following Table 1, the values on the upper and lower lines in the column of Elementary analysis for each compound are calculated and found values, respectively.

TABLE 1

| Compound No. | Chemical formula | Physicochemical properties | Elementary analysis H | C | N |
|---|---|---|---|---|---|
| 1 | (structure) | m.p. 55~57° C. | 7.10 / 7.30 | 75.81 / 76.00 | 5.20 / 5.25 |
| 2 | (structure) | m.p. 73~76° C. | 7.47 / 7.50 | 76.29 / 76.40 | 4.94 / 5.00 |
| 3 | (structure) | $n_D^{21}$ 1.5520 | 7.47 / 7.40 | 76.29 / 76.00 | 4.94 / 4.60 |
| 4 | (structure) | m.p. 82~84° C. | 7.47 / 7.60 | 76.29 / 75.57 | 4.94 / 4.87 |
| 5 | (structure) | m.p. 55~57° C. | 7.47 / 7.56 | 76.29 / 76.02 | 4.94 / 4.91 |
| 6 | (structure) | m.p. 89~90° C. | 7.47 / 7.64 | 76.29 / 76.57 | 4.94 / 4.94 |
| 7 | (structure) | m.p. 75~77° C. | 7.07 / 7.22 | 72.21 / 72.36 | 4.68 / 4.63 |

TABLE 1-continued

| Compound No. | Chemical formula | Physicochemical properties | Elementary analysis H | C | N |
|---|---|---|---|---|---|
| 8 | Ph-O-CH(C$_2$H$_5$)-CONH-CH$_2$-C$_6$H$_4$-OCH$_3$ (m-) | m.p. 55~57° C. | 7.07<br>7.27 | 72.21<br>72.46 | 4.68<br>4.64 |
| 9 | Ph-O-CH(C$_2$H$_5$)-CONH-CH$_2$-C$_6$H$_4$-OCH$_3$ (p-) | m.p. 80~82° C. | 7.07<br>7.34 | 72.21<br>71.95 | 4.68<br>4.44 |
| 10 | Ph-O-CH(C$_2$H$_5$)-CONH-CH$_2$-C$_6$H$_4$-Cl (m-) | m.p. 66~68° C. | 5.97<br>6.00 | 67.21<br>67.37 | 4.61<br>4.68 |
| 11 | Ph-O-CH(C$_2$H$_5$)-CONH-CH$_2$-C$_6$H$_4$-Cl (p-) | m.p. 87~89° C. | 5.97<br>6.00 | 67.21<br>66.95 | 4.61<br>4.60 |
| 12 | (2-CH$_3$)C$_6$H$_4$-O-CH(C$_2$H$_5$)-CONH-CH$_2$-C$_6$H$_5$ | m.p. 61~63° C. | 7.47<br>7.47 | 76.29<br>75.52 | 4.94<br>4.89 |
| 13 | (2-CH$_3$)C$_6$H$_4$-O-CH(C$_2$H$_5$)-CONH-CH$_2$-C$_6$H$_4$-CH$_3$ (p-) | m.p. 75~77° C. | 7.80<br>7.82 | 76.73<br>75.84 | 4.71<br>4.92 |
| 14 | (2-CH$_3$)C$_6$H$_4$-O-CH(C$_2$H$_5$)-CONH-CH$_2$-C$_6$H$_4$-OCH$_3$ (p-) | m.p. 68~70° C. | 7.40<br>7.49 | 72.82<br>72.69 | 4.47<br>4.70 |
| 15 | (2-CH$_3$)C$_6$H$_4$-O-CH(C$_2$H$_5$)-CONH-CH$_2$-C$_6$H$_4$-Cl (p-) | m.p. 69~71° C. | 6.34<br>6.42 | 68.02<br>68.39 | 4.41<br>4.43 |
| 16 | (3-CH$_3$)C$_6$H$_4$-O-CH(C$_2$H$_5$)-CONH-CH$_2$-C$_6$H$_5$ | m.p. 66~68° C. | 7.74<br>7.44 | 76.29<br>75.50 | 4.94<br>5.10 |
| 17 | (3-CH$_3$)C$_6$H$_4$-O-CH(C$_2$H$_5$)-CONH-CH$_2$-C$_6$H$_4$-CH$_3$ (p-) | m.p. 89~91° C. | 7.80<br>7.91 | 76.73<br>76.73 | 4.71<br>4.93 |

TABLE 1-continued

| Compound No. | Chemical formula | Physicochemical properties | Elementary analysis H | C | N |
|---|---|---|---|---|---|
| 18 | 3-CH₃-C₆H₄-OCH(C₂H₅)CONHCH₂-C₆H₄-4-OCH₃ | m.p. 55~57° C. | 7.40<br>7.45 | 72.82<br>72.64 | 4.47<br>4.44 |
| 19 | 4-CH₃-C₆H₄-OCH(C₂H₅)CONHCH₂-C₆H₄-4-OCH₃ | m.p. 70~71° C. | 7.47<br>7.80 | 76.29<br>76.59 | 4.94<br>5.03 |
| 20 | 4-CH₃-C₆H₄-OCH(C₂H₅)CONHCH₂-C₆H₄-4-CH₃ | m.p. 81~83° C. | 7.80<br>7.85 | 76.73<br>76.90 | 4.71<br>4.80 |
| 21 | 4-CH₃-C₆H₄-OCH(C₂H₅)CONHCH₂-C₆H₄-4-OCH₃ | m.p. 85~87° C. | 7.40<br>7.20 | 72.82<br>73.11 | 4.47<br>4.56 |
| 22 | 4-CH₃-C₆H₄-OCH(C₂H₅)CONHCH₂-C₆H₄-4-Cl | m.p. 65~67° C. | 6.34<br>6.57 | 68.02<br>68.20 | 4.41<br>4.30 |
| 23 | 2,3-(CH₃)₂-C₆H₃-OCH(C₂H₅)CONHCH₂-C₆H₅ | m.p. 102~104° C. | 7.80<br>7.87 | 76.73<br>76.53 | 4.71<br>4.67 |
| 24 | 2,3-(CH₃)₂-C₆H₃-OCH(C₂H₅)CON(CH₃)CH₂-C₆H₅ | b.p. 172~175° C./3 mm | 8.09<br>8.20 | 77.13<br>77.20 | 4.50<br>4.65 |
| 25 | 2,3-(CH₃)₂-C₆H₃-OCH(C₂H₅)CONHCH₂-C₆H₄-2-CH₃ | m.p. 98~99° C. | 8.09<br>8.19 | 77.13<br>77.03 | 4.50<br>4.47 |
| 26 | 2,3-(CH₃)₂-C₆H₃-OCH(C₂H₅)CONHCH₂-C₆H₄-2-OCH₃ | m.p. 68~70° C. | 7.70<br>7.82 | 73.36<br>73.32 | 4.28<br>4.34 |
| 27 | 3,4-(CH₃)₂-C₆H₃-OCH(C₂H₅)CONHCH₂-C₆H₅ | m.p. 78~79° C. | 7.80<br>8.02 | 76.73<br>77.27 | 4.71<br>4.76 |

TABLE 1-continued

| Compound No. | Chemical formula | Physicochemical properties | Elementary analysis H C N |
|---|---|---|---|
| 28 | 3,4-dimethylphenyl-O-CH(C₂H₅)-CONH-CH₂-(3-methylphenyl) | m.p. 73~76° C. | 8.09 77.13 4.50<br>8.25 77.10 4.54 |
| 29 | 3,4-dimethylphenyl-O-CH(C₂H₅)-CONH-CH₂-(2-methoxyphenyl) | m.p. 91~92° C. | 7.70 73.36 4.28<br>7.80 73.41 4.30 |
| 30 | 3,5-dimethylphenyl-O-CH(C₂H₅)-CONH-CH₂-phenyl | m.p. 93~94° C. | 7.80 76.73 4.71<br>7.94 76.91 4.71 |
| 31 | 3,5-dimethylphenyl-O-CH(C₂H₅)-CON(CH₃)-CH₂-phenyl | $n_D^{25.0}$ 1.5491 | 8.09 77.13 4.50<br>8.36 77.72 4.56 |
| 32 | 3,5-dimethylphenyl-O-CH(C₂H₅)-CONH-CH₂-(2-methylphenyl) | m.p. 114~116° C. | 8.09 77.13 4.50<br>8.41 77.09 4.33 |
| 33 | 3,5-dimethylphenyl-O-CH(C₂H₅)-CONH-CH₂-(3-methylphenyl) | m.p. 80~82° C. | 8.09 77.13 4.50<br>7.88 76.94 4.63 |
| 34 | 3,5-dimethylphenyl-O-CH(C₂H₅)-CONH-CH₂-(4-methylphenyl) | m.p. 112~113° C. | 8.09 77.13 4.50<br>8.30 77.87 4.47 |
| 35 | 3,5-dimethylphenyl-O-CH(C₂H₅)-CONH-CH₂-(2-methoxyphenyl) | m.p. 82~84° C. | 7.70 73.36 4.28<br>7.92 74.02 4.35 |

TABLE 1-continued

| Compound No. | Chemical formula | Physicochemical properties | Elementary analysis H | C | N |
|---|---|---|---|---|---|
| 36 | 3,5-(CH₃)₂-C₆H₃-O-CH(C₂H₅)-CONH-CH₂-C₆H₄-OCH₃(3) | m.p. 103~105° C. | 7.70<br>7.51 | 73.36<br>73.66 | 4.28<br>4.27 |
| 37 | 3,5-(CH₃)₂-C₆H₃-O-CH(C₂H₅)-CONH-CH₂-C₆H₄-OCH₃(4) | m.p. 82~84° C. | 7.70<br>8.06 | 73.36<br>73.59 | 4.28<br>4.12 |
| 38 | 3,5-(CH₃)₂-C₆H₃-O-CH(C₂H₅)-CONH-CH₂-C₆H₄-Cl(2) | m.p. 93~95° C. | 6.68<br>6.99 | 68.77<br>69.00 | 4.22<br>4.42 |
| 39 | 3,5-(CH₃)₂-C₆H₃-O-CH(C₂H₅)-CON(CH₂-CH=CH₂)(CH₂-C₆H₄-Cl(2)) | $n_D^{25.8}$ 1.5522 | 7.05<br>7.40 | 71.05<br>70.83 | 3.77<br>3.86 |
| 40 | 3,5-(CH₃)₂-C₆H₃-O-CH(C₂H₅)-CONH-CH₂-C₆H₄-Cl(4) | m.p. 100~102° C. | 6.68<br>6.92 | 68.77<br>68.91 | 4.22<br>4.51 |
| 41 | 3,5-(CH₃)₂-C₆H₃-O-CH(C₃H₇-n)-CONH-CH₂-C₆H₅ | m.p. 94~97° C. | 8.09<br>7.84 | 77.13<br>76.70 | 4.50<br>4.67 |
| 42 | 2,4-(CH₃)₂-C₆H₃-O-CH(C₂H₅)-CONH-CH₂-C₆H₅ | m.p. 80~83° C. | 7.80<br>7.81 | 76.73<br>77.16 | 4.71<br>4.72 |
| 43 | 2,4-(CH₃)₂-C₆H₃-O-CH(C₂H₅)-CONH-CH₂-C₆H₄-OCH₃(2) | m.p. 89~90° C. | 7.70<br>7.73 | 73.36<br>72.86 | 4.28<br>4.26 |

TABLE 1-continued

| Compound No. | Chemical formula | Physicochemical properties | Elementary analysis H | C | N |
|---|---|---|---|---|---|
| 44 | CH$_3$-(2,4-dimethylphenyl)-O-CH(C$_2$H$_5$)CONHCH$_2$-(4-methylphenyl) with 2-CH$_3$ | m.p. 80~91° C. | 8.09 / 8.10 | 77.13 / 76.55 | 4.53 / 4.53 |
| 45 | CH$_3$-(2,4-dimethylphenyl)-O-CH(C$_2$H$_5$)CONHCH$_2$-(4-Cl-phenyl) | m.p. 63~65° C. | 6.68 / 6.76 | 68.77 / 69.03 | 4.22 / 4.24 |
| 46 | Cl-(4-chloro-2-methylphenyl)-O-CH(C$_2$H$_5$)CONHCH$_2$-phenyl | m.p. 98~99° C. | 6.34 / 6.40 | 68.02 / 68.05 | 4.41 / 4.30 |
| 47 | CH$_3$-(4-methyl-3-chlorophenyl)-O-CH(C$_2$H$_5$)CONHCH$_2$-phenyl | m.p. 93~95° C. | 6.34 / 6.37 | 68.02 / 68.12 | 4.41 / 4.39 |
| 48 | CH$_3$-(4-methyl-3-chlorophenyl)-O-CH(C$_2$H$_5$)CONHCH$_2$-(2-methylphenyl) | m.p. 99~101° C. | 6.68 / 6.73 | 68.77 / 68.14 | 4.22 / 4.16 |
| 49 | Cl-(4-chloro-3-methylphenyl)-O-CH(C$_2$H$_5$)CONHCH$_2$-phenyl | m.p. 95~97° C. | 6.34 / 6.72 | 68.02 / 68.41 | 4.19 / 4.19 |
| 50 | Cl-(4-chloro-3-methylphenyl)-O-CH(C$_2$H$_5$)CON(CH$_3$)CH$_2$-phenyl | $n_D^{25.6}$ 1.5579 | 6.68 / 7.05 | 68.77 / 69.26 | 4.22 / 3.86 |
| 51 | Cl-(4-chloro-3-methylphenyl)-O-CH(C$_2$H$_5$)CONHCH$_2$-(2-methylphenyl) | m.p. 115~117° C. | 6.68 / 6.88 | 68.77 / 68.48 | 4.22 / 3.96 |
| 52 | Cl-(4-chloro-3-methylphenyl)-O-CH(C$_2$H$_5$)CONHCH$_2$-(3-methylphenyl) | m.p. 88~90° C. | 6.68 / 6.89 | 68.77 / 68.89 | 4.22 / 4.10 |

TABLE 1-continued

| Compound No. | Chemical formula | Physicochemical properties | Elementary analysis H | C | N |
|---|---|---|---|---|---|
| 53 | 4-Cl, 3-CH₃-phenyl-O-CH(C₂H₅)-CONH-CH₂-(4-CH₃-phenyl) | m.p. 113~115° C. | 6.68<br>7.00 | 68.77<br>68.48 | 4.22<br>3.95 |
| 54 | 4-Cl, 3-CH₃-phenyl-O-CH(n-C₃H₇)-CONH-CH₂-phenyl | m.p. 75~78° C. | 6.68<br>6.72 | 68.77<br>68.09 | 4.22<br>4.30 |
| 55 | 4-Cl, 3,5-(CH₃)₂-phenyl-O-CH(C₂H₅)-CONH-CH₂-phenyl | m.p. 111~113° C. | 6.68<br>6.75 | 68.77<br>68.62 | 4.22<br>4.11 |
| 56 | 4-Cl, 3,5-(CH₃)₂-phenyl-O-CH(C₂H₅)-CON(CH₃)-CH₂-phenyl | $n_D^{25.2}$ 1.5561 | 6.99<br>7.16 | 69.44<br>69.46 | 4.05<br>3.89 |
| 57 | 4-Cl, 3,5-(CH₃)₂-phenyl-O-CH(C₂H₅)-CON(i-C₃H₇)-CH₂-phenyl | m.p. 93~95° C. | 7.55<br>7.33 | 70.67<br>71.42 | 3.75<br>3.89 |
| 58 | 4-Cl, 3,5-(CH₃)₂-phenyl-O-CH(C₂H₅)-CONH-CH₂-(2-CH₃-phenyl) | m.p. 143~144° C. | 6.99<br>6.98 | 69.44<br>68.77 | 4.05<br>4.07 |
| 59 | 4-Cl, 3,5-(CH₃)₂-phenyl-O-CH(C₂H₅)-CONH-CH₂-(4-CH₃-phenyl) | m.p. 123~124° C. | 6.99<br>7.23 | 69.44<br>69.77 | 4.05<br>4.12 |
| 60 | 4-Cl, 3,5-(CH₃)₂-phenyl-O-CH(C₂H₅)-CONH-CH₂-(2-OCH₃-phenyl) | m.p. 107~108° C. | 6.68<br>6.66 | 66.37<br>66.00 | 3.87<br>3.87 |
| 61 | 4-Cl, 3,5-(CH₃)₂-phenyl-O-CH(n-C₃H₇)-CONH-CH₂-phenyl | m.p. 111~113° C. | 6.99<br>7.01 | 69.45<br>69.16 | 4.05<br>4.12 |

TABLE 1-continued

| Compound No. | Chemical formula | Physicochemical properties | Elementary analysis H | C | N |
|---|---|---|---|---|---|
| 62 | 2-Cl-C₆H₄-O-CH(C₂H₅)-CONH-CH₂-C₆H₅ | m.p. 78~79° C. | 5.97<br>5.92 | 67.21<br>67.04 | 4.61<br>4.63 |
| 63 | 2-Cl-C₆H₄-O-CH(C₂H₅)-CON(CH₃)-CH₂-C₆H₅ | $n_D^{24.4}$ 1.5586 | 6.34<br>6.46 | 68.02<br>68.41 | 4.41<br>4.19 |
| 64 | 2-Cl-C₆H₄-O-CH(C₂H₅)-CONH-CH₂-(2-CH₃-C₆H₄) | m.p. 94~96° C. | 6.34<br>6.34 | 68.02<br>67.38 | 4.41<br>4.38 |
| 65 | 2-Cl-C₆H₄-O-CH(C₂H₅)-CONH-CH₂-(3-OCH₃-C₆H₄) | m.p. 86~87° C. | 6.04<br>6.07 | 64.76<br>64.54 | 4.20<br>4.30 |
| 66 | 2-Cl-C₆H₄-O-CH(C₂H₅)-CONH-CH₂-(4-OCH₃-C₆H₄) | m.p. 75~78° C. | 6.04<br>6.10 | 64.76<br>64.91 | 4.20<br>4.19 |
| 67 | 3-Cl-C₆H₄-O-CH(C₂H₅)-CONH-CH₂-C₆H₅ | m.p. 74~76° C. | 5.97<br>6.10 | 67.21<br>67.40 | 4.61<br>4.50 |
| 68 | 3-Cl-C₆H₄-O-CH(C₂H₅)-CONH-CH(CH₃)-C₆H₅ | m.p. 89~91° C. | 6.34<br>6.40 | 68.02<br>68.30 | 4.41<br>4.20 |
| 69 | 3-Cl-C₆H₄-O-CH(C₂H₅)-CONH-CH(C₂H₅)-C₆H₅ | $n_D^{26.0}$ 1.5661 | 6.68<br>6.50 | 68.77<br>69.12 | 4.22<br>4.40 |
| 70 | 3-Cl-C₆H₄-O-CH(C₂H₅)-CON(CH₃)-CH₂-C₆H₅ | $n_D^{22}$ 1.5611 | 6.34<br>6.40 | 68.02<br>67.90 | 4.41<br>4.00 |

TABLE 1-continued

| Compound No. | Chemical formula | Physicochemical properties | Elementary analysis H | C | N |
|---|---|---|---|---|---|
| 71 | 3-Cl-C6H4-OCH(C2H5)CON(C2H5)(CH2-C6H5) | $n_D^{26}$ 1.5516 | 6.68 6.55 | 68.77 67.76 | 4.22 4.07 |
| 72 | 3-Cl-C6H4-OCH(C2H5)CON(CH2-CH=CH2)(CH2-C6H5) | $n_D^{26}$ 1.5575 | 6.45 6.46 | 69.86 69.45 | 4.07 3.93 |
| 73 | 3-Cl-C6H4-OCH(C2H5)CON(OCH3)(CH2-C6H5) | $n_D^{26}$ 1.5526 | 6.04 6.02 | 64.76 64.22 | 4.20 4.25 |
| 74 | 3-Cl-C6H4-OCH(C2H5)CONHCH2-(2-CH3-C6H4) | m.p. 93~95° C. | 6.34 6.60 | 68.02 68.10 | 4.41 4.20 |
| 75 | 3-Cl-C6H4-OCH(C2H5)CONHCH2-(3-CH3-C6H4) | m.p. 74~76° C. | 6.34 6.30 | 68.02 68.00 | 4.41 4.20 |
| 76 | 3-Cl-C6H4-OCH(C2H5)CONHCH2-(4-CH3-C6H4) | m.p. 88~90° C. | 6.34 6.40 | 68.02 68.10 | 4.41 4.20 |
| 77 | 3-Cl-C6H4-OCH(C2H5)CONHCH2-(2-CH3O-C6H4) | m.p. 73~76° C. | 6.04 6.06 | 64.76 64.50 | 4.20 4.13 |
| 78 | 3-Cl-C6H4-OCH(C2H5)CONHCH2-(3-CH3O-C6H4) | $n_D^{23}$ 1.5646 | 6.04 5.96 | 64.76 64.90 | 4.20 3.94 |
| 79 | 3-Cl-C6H4-OCH(C2H5)CONHCH2-(4-CH3O-C6H4) | $n_D^{23}$ 1.5619 | 6.04 6.02 | 64.76 64.66 | 4.20 3.95 |
| 80 | 3-Cl-C6H4-OCH(C2H5)CONHCH2-(4-OC2H5-C6H4) | m.p. 40~42° C. | 6.38 6.10 | 65.60 65.40 | 4.03 3.80 |

TABLE 1-continued

| Compound No. | Chemical formula | Physicochemical properties | Elementary analysis H | C | N |
|---|---|---|---|---|---|
| 81 | 3-Cl-C6H4-OCH(C2H5)CONHCH2-C6H4-2-Cl | m.p. 80~82° C. | 5.07<br>5.01 | 60.36<br>59.82 | 4.14<br>4.13 |
| 82 | 3-Cl-C6H4-OCH(C2H5)CONHCH2-C6H4-3-Cl | $n_D^{26}$ 1.5695 | 5.07<br>5.06 | 60.36<br>60.42 | 4.14<br>3.94 |
| 83 | 3-Cl-C6H4-OCH(CH(CH3)2)CONHCH2-C6H5 | $n_D^{22.0}$ 1.5516 | 6.34<br>6.60 | 68.02<br>67.80 | 4.41<br>4.30 |
| 84 | 3-Cl-C6H4-OCH(n-C3H7)CONHCH2-C6H5 | $a_D^{24.0}$ 1.5557 crystallized on the air after treatment | 6.34<br>6.50 | 68.02<br>67.83 | 4.41<br>4.20 |
| 85 | 4-Cl-C6H4-OCH(C2H5)CONHCH2-C6H5 | m.p. 80~90° C. | 5.97<br>6.10 | 67.21<br>67.20 | 4.61<br>4.30 |
| 86 | 4-Cl-C6H4-OCH(C2H5)CONHCH(CH3)-C6H5 | m.p. 85~88° C. | 6.34<br>6.30 | 68.02<br>68.20 | 4.41<br>4.20 |
| 87 | 4-Cl-C6H4-OCH(C2H5)CON(C2H5)(CH2-C6H5) | m.p. 68~70° C. | 6.68<br>6.76 | 68.77<br>68.50 | 4.22<br>4.25 |
| 88 | 4-Cl-C6H4-OCH(C2H5)CON(CH2-CH=CH2)(CH2-C6H5) | $n_D^{24.6}$ 1.5620 | 6.45<br>6.60 | 69.86<br>69.99 | 4.07<br>4.08 |
| 89 | 4-Cl-C6H4-OCH(C2H5)CON(i-C3H7)(CH2-C6H5) | b.p. 177° C./3 mm | 6.99<br>6.99 | 69.45<br>69.27 | 4.05<br>3.75 |
| 90 | 3,4-Cl2-C6H3-OCH(C2H5)CONHCH2-C6H4-2-CH3 | m.p. 108~109° C. | 6.34<br>6.30 | 68.02<br>68.20 | 4.41<br>4.20 |

TABLE 1-continued
| Compound No. | Chemical formula | Physicochemical properties | Elementary analysis H | C | N |
|---|---|---|---|---|---|
| 91 | 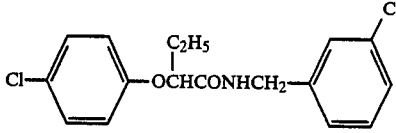 | m.p. 91~93° C. | 6.34<br>6.30 | 68.02<br>68.10 | 4.41<br>4.10 |
| 92 | 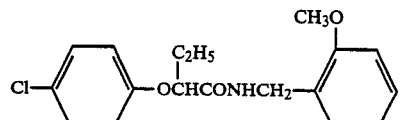 | m.p. 101~102° C. | 6.04<br>6.10 | 64.76<br>64.75 | 4.20<br>4.35 |
| 93 | 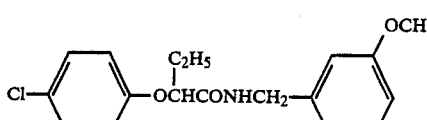 | m.p. 95~97° C. | 6.04<br>6.16 | 64.76<br>64.77 | 4.20<br>4.28 |
| 94 | 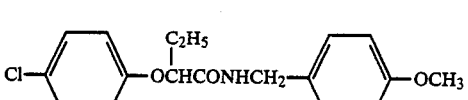 | m.p. 98~100° C. | 6.04<br>6.02 | 64.76<br>64.47 | 4.20<br>4.13 |
| 95 | 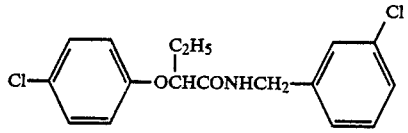 | m.p. 105~106° C. | 5.07<br>5.10 | 60.37<br>60.20 | 4.14<br>4.00 |
| 96 | 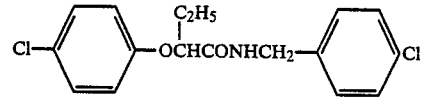 | m.p. 92~93° C. | 5.07<br>5.14 | 60.37<br>60.30 | 4.14<br>4.10 |
| 97 | 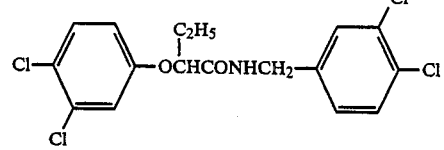 | m.p. 89~90° C. | 4.33<br>4.33 | 54.79<br>54.51 | 3.76<br>3.79 |
| 98 | 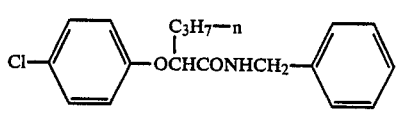 | m.p. 67~70° C. | 6.34<br>6.54 | 68.02<br>67.96 | 4.41<br>4.60 |
| 99 | 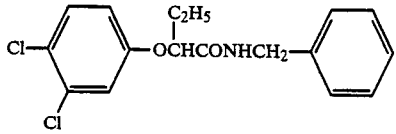 | m.p. 108~110° C. | 5.07<br>4.90 | 60.36<br>60.10 | 4.14<br>4.00 |
| 100 | 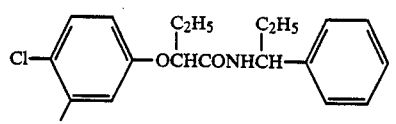 | $n_D^{26.0}$ 1.5608 | 5.44<br>5.40 | 61.37<br>61.10 | 3.98<br>3.80 |
| 101 | 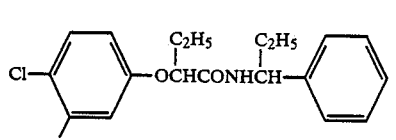 | $n_D^{26.0}$ 1.5548 | 5.78<br>5.92 | 62.30<br>62.31 | 3.82<br>3.70 |

TABLE 1-continued

| Compound No. | Chemical formula | Physicochemical properties | Elementary analysis H | C | N |
|---|---|---|---|---|---|
| 102 | 3,4-Cl$_2$-C$_6$H$_3$-OCH(C$_2$H$_5$)CON(CH$_3$)(CH$_2$C$_6$H$_5$) | $n_D^{22.0}$ 1.5683 | 5.44<br>5.50 | 61.37<br>61.50 | 3.98<br>4.00 |
| 103 | 3,4-Cl$_2$-C$_6$H$_3$-OCH(C$_2$H$_5$)CON(CH$_2$-CH=CH$_2$)(CH$_2$C$_6$H$_5$) | $n_D^{25.6}$ 1.5652 | 5.60<br>5.70 | 63.50<br>63.76 | 3.70<br>3.66 |
| 104 | 3,4-Cl$_2$-C$_6$H$_3$-OCH(C$_2$H$_5$)CON(OCH$_3$)(CH$_2$C$_6$H$_5$) | $n_D^{25.6}$ 1.5580 | 5.20<br>5.12 | 58.71<br>58.98 | 3.80<br>3.65 |
| 105 | 3,4-Cl$_2$-C$_6$H$_3$-OCH(C$_2$H$_5$)CONHCH$_2$-(2-CH$_3$-C$_6$H$_4$) | m.p. 122~124° C. | 5.44<br>5.50 | 61.37<br>61.50 | 3.98<br>4.00 |
| 106 | 3,4-Cl$_2$-C$_6$H$_3$-OCH(C$_2$H$_5$)CONHCH$_2$-(3-CH$_3$-C$_6$H$_4$) | m.p. 101~103° C. | 5.44<br>5.40 | 61.37<br>61.50 | 3.98<br>3.80 |
| 107 | 3,4-Cl$_2$-C$_6$H$_3$-OCH(C$_2$H$_5$)CONHCH$_2$-(4-CH$_3$-C$_6$H$_4$) | m.p. 113~114° C. | 5.44<br>5.50 | 61.37<br>61.50 | 3.98<br>3.80 |
| 108 | 3,4-Cl$_2$-C$_6$H$_3$-OCH(C$_2$H$_5$)CONHCH$_2$-(2-CH$_3$O-C$_6$H$_4$) | m.p. 91~93° C. | 5.46<br>5.25 | 58.54<br>58.31 | 3.79<br>3.71 |
| 109 | 3,4-Cl$_2$-C$_6$H$_3$-OCH(C$_2$H$_5$)CONHCH$_2$-(3-OCH$_3$-C$_6$H$_4$) | m.p. 104~105° C. | 5.46<br>5.16 | 58.54<br>58.53 | 3.79<br>3.81 |
| 110 | 3,4-Cl$_2$-C$_6$H$_3$-OCH(C$_2$H$_5$)CONHCH$_2$-(3-OCH$_3$-4-OCH$_3$-C$_6$H$_3$) | m.p. 108~110° C. | 5.32<br>5.33 | 57.29<br>56.98 | 3.52<br>3.34 |

TABLE 1-continued

| Compound No. | Chemical formula | Physicochemical properties | Elementary analysis H | C | N |
|---|---|---|---|---|---|
| 111 | 3,4-Cl$_2$-C$_6$H$_3$-OCH(C$_2$H$_5$)CONHCH$_2$-C$_6$H$_4$-3-Cl | m.p. 87~89° C. | 4.33<br>4.36 | 54.78<br>54.64 | 3.76<br>3.38 |
| 112 | 3,4-Cl$_2$-C$_6$H$_3$-OCH(n-C$_3$H$_7$)CONHCH$_2$-C$_6$H$_5$ | n$_D^{24.4}$ 1.5632 crystallized after treatment | 5.44<br>5.63 | 61.37<br>61.57 | 3.98<br>4.25 |
| 113 | 3,5-Cl$_2$-C$_6$H$_3$-OCH(C$_2$H$_5$)CONHCH$_2$-C$_6$H$_5$ | m.p. 122~124° C. | 5.07<br>5.11 | 60.36<br>60.69 | 4.14<br>4.19 |
| 114 | 3,5-Cl$_2$-C$_6$H$_3$-OCH(C$_2$H$_5$)CONHCH(CH$_3$)-C$_6$H$_5$ | m.p. 100~102° C. | 5.44<br>5.40 | 61.37<br>61.18 | 3.98<br>3.98 |
| 115 | 3,5-Cl$_2$-C$_6$H$_3$-OCH(C$_2$H$_5$)CON(CH$_3$)CH$_2$-C$_6$H$_5$ | n$_D^{25.0}$ 1.5669 | 5.44<br>5.50 | 61.37<br>61.50 | 3.98<br>4.00 |
| 116 | 3,5-Cl$_2$-C$_6$H$_3$-OCH(C$_2$H$_5$)CONHCH$_2$-C$_6$H$_4$-2-CH$_3$ | m.p. 135~137° C. | 5.44<br>5.45 | 61.37<br>61.50 | 3.98<br>3.96 |
| 117 | 3,5-Cl$_2$-C$_6$H$_3$-OCH(C$_2$H$_5$)COPNHCH$_2$-C$_6$H$_4$-4-OCH$_3$ | m.p. 128~129° C. | 5.46<br>5.25 | 58.54<br>58.80 | 3.79<br>3.86 |
| 118 | 3,5-Cl$_2$-C$_6$H$_3$-OCH(C$_2$H$_5$)CONHCH$_2$-C$_6$H$_4$-2-Cl | m.p. 141~142° C. | 4.33<br>4.33 | 54.78<br>54.50 | 3.76<br>3.71 |
| 119 | 3,5-Cl$_2$-C$_6$H$_3$-OCH(C$_2$H$_5$)CONHCH$_2$-C$_6$H$_4$-3-Cl | m.p. 119~121° C. | 4.33<br>4.33 | 54.78<br>54.92 | 3.76<br>3.82 |

TABLE 1-continued

| Compound No. | Chemical formula | Physicochemical properties | Elementary analysis H | C | N |
|---|---|---|---|---|---|
| 120 | 3,5-Cl₂-C₆H₃-O-CH(C₃H₇-n)-CONH-CH₂-C₆H₅ | m.p. 102~104° C. | 5.44<br>5.46 | 61.37<br>61.20 | 3.98<br>4.10 |
| 121 | 2,4-Cl₂-C₆H₃-O-CH(C₂H₅)-CONH-CH₂-C₆H₅ | m.p. 104~106° C. | 5.07<br>5.00 | 60.36<br>60.40 | 4.14<br>4.10 |
| 122 | 2,6-Cl₂-C₆H₃-O-CH(C₂H₅)-CONH-CH₂-C₆H₅ | m.p. 86~87° C. | 5.07<br>5.10 | 60.36<br>60.50 | 4.14<br>4.00 |
| 123 | C₆H₅-O-CH(C₂H₅)-CONH-CH₂-(2-furyl) | $n_D^{25.6}$ 1.5362 | 6.61<br>6.65 | 69.48<br>69.44 | 5.40<br>5.23 |
| 124 | C₆H₅-O-CH(C₂H₅)-CONH-CH₂-(2-thienyl) | $n_D^{25.6}$ 1.5658 | 6.22<br>6.18 | 65.42<br>65.57 | 5.09<br>4.92 |
| 125 | 3-CH₃-C₆H₄-O-CH(C₂H₅)-CONH-CH₂-(2-furyl) | m.p. 62~64° C. | 7.01<br>6.98 | 70.31<br>69.97 | 5.13<br>4.98 |
| 126 | 3,4-(CH₃)₂-C₆H₃-O-CH(C₂H₅)-CONH-CH₂-(2-thienyl) | m.p. 76~80° C. | 6.98<br>7.04 | 67.29<br>67.22 | 4.62<br>4.55 |
| 127 | 3,5-(CH₃)₂-C₆H₃-O-CH(C₂H₅)-CONH-CH₂-(2-furyl) | m.p. 78~80° C. | 7.37<br>7.14 | 71.05<br>70.86 | 4.87<br>4.97 |
| 128 | 3,5-(CH₃)₂-C₆H₃-O-CH(C₂H₅)-CONH-CH₂-(2-thienyl) | m.p. 84~86° C. | 6.98<br>7.08 | 67.29<br>66.98 | 4.62<br>4.49 |

TABLE 1-continued

| Compound No. | Chemical formula | Physicochemical properties | Elementary analysis H | C | N |
|---|---|---|---|---|---|
| 129 | 3,5-dimethylphenyl-O-CH($C_2H_5$)-CONHCH$_2$-(2-pyridyl) | m.p. 71~73° C. | 7.43<br>7.43 | 72.45<br>72.29 | 9.39<br>9.29 |
| 130 | 3,5-dimethylphenyl-O-CH($C_2H_5$)-CONHCH$_2$-(3-pyridyl) | m.p. 94~97° C. | 7.43<br>7.47 | 72.45<br>72.17 | 9.39<br>9.16 |
| 131 | 3-chloro-4-methylphenyl-O-CH($C_2H_5$)-CONHCH$_2$-(2-furyl) | m.p. 54~56° C. | 5.89<br>5.91 | 62.43<br>62.26 | 4.55<br>4.51 |
| 132 | 3-chloro-4-methylphenyl-O-CH($C_2H_5$)-CONHCH$_2$-(2-thienyl) | m.p. 77~79° C. | 5.60<br>5.58 | 59.34<br>59.14 | 4.33<br>4.35 |
| 133 | 4-chloro-3-methylphenyl-O-CH($C_2H_5$)-CONHCH$_2$-(2-furyl) | m.p. 100~102° C. | 5.89<br>6.13 | 62.43<br>62.70 | 4.55<br>4.35 |
| 134 | 4-chloro-3-methylphenyl-O-CH($C_2H_5$)-CONHCH$_2$-(2-thienyl) | m.p. 89~91° C. | 5.60<br>5.89 | 59.34<br>59.55 | 4.33<br>4.13 |
| 135 | 4-chloro-3-methylphenyl-O-CH($C_2H_5$)-CONHCH$_2$-(2-pyridyl) | m.p. 58~60° C. | 6.01<br>6.29 | 64.04<br>64.25 | 8.79<br>8.53 |
| 136 | 4-chloro-3,5-dimethylphenyl-O-CH($C_2H_5$)-CONHCH$_2$-(2-furyl) | m.p. 101~102° C. | 6.26<br>6.36 | 63.45<br>63.45 | 4.35<br>4.24 |
| 137 | 4-chloro-3,5-dimethylphenyl-O-CH($C_2H_5$)-CONHCH$_2$-(2-thienyl) | m.p. 105~107° C. | 5.97<br>6.00 | 60.43<br>60.04 | 4.15<br>4.09 |

TABLE 1-continued

| Compound No. | Chemical formula | Physicochemical properties | Elementary analysis H | C | N |
|---|---|---|---|---|---|
| 138 | 4-Cl-3,5-(CH$_3$)$_2$-C$_6$H$_2$-OCH(C$_2$H$_5$)CONHCH$_2$-(2-pyridyl) | m.p. 99~101° C. | 6.36 6.39 | 64.96 64.90 | 8.42 8.47 |
| 139 | 4-Cl-3,5-(CH$_3$)$_2$-C$_6$H$_2$-OCH(C$_2$H$_5$)CONHCH$_2$-(3-pyridyl) | m.p. 88~92° C. | 6.36 6.44 | 64.96 64.80 | 8.42 8.37 |
| 140 | 4-Cl-3,5-(CH$_3$)$_2$-C$_6$H$_2$-OCH(C$_2$H$_5$)CONHCH$_2$-(4-pyridyl) | m.p. 128~129° C. | 6.36 6.37 | 64.96 64.73 | 8.42 8.42 |
| 141 | 2-Cl-C$_6$H$_4$-OCH(C$_2$H$_5$)CONHCH$_2$-(2-thienyl) | m.p. 79~80° C. | 5.21 5.28 | 58.15 57.89 | 4.52 4.61 |
| 142 | 3-Cl-C$_6$H$_4$-OCH(C$_2$H$_5$)CONHCH$_2$-(2-furyl) | $n_D^{26}$ 1.5433 | 5.49 5.50 | 61.33 61.05 | 4.77 4.48 |
| 143 | 3-Cl-C$_6$H$_4$-OCH(C$_2$H$_5$)CONHCH$_2$-(2-thienyl) | m.p. 52~54° C. | 5.21 5.20 | 58.15 57.94 | 4.52 4.52 |
| 144 | 3-Cl-C$_6$H$_4$-OCH(C$_2$H$_5$)CONHCH$_2$-(2-pyridyl) | $n_D^{26}$ 1.5610 | 5.62 5.64 | 63.05 62.83 | 9.19 8.99 |
| 145 | 3-Cl-C$_6$H$_4$-OCH(C$_2$H$_5$)CONHCH$_2$-(3-pyridyl) | $n_D^{26}$ 1.5626 | 5.62 5.71 | 63.05 62.86 | 9.19 8.89 |
| 146 | 3-Cl-C$_6$H$_4$-OCH(C$_2$H$_5$)CONHCH$_2$-(4-pyridyl) | $n_D^{26}$ 1.5618 | 5.62 5.72 | 63.05 62.93 | 9.19 9.07 |
| 147 | 4-Cl-C$_6$H$_4$-OCH(C$_2$H$_5$)CONHCH$_2$-(2-furyl) | m.p. 88~89° C. | 5.49 5.48 | 61.33 61.36 | 4.77 4.90 |

TABLE 1-continued

| Compound No. | Chemical formula | Physicochemical properties | Elementary analysis H | C | N |
|---|---|---|---|---|---|
| 148 | 4-Cl-C6H4-O-CH(C2H5)-CONHCH2-(2-thienyl) | m.p. 97~100° C. | 5.21<br>5.24 | 58.15<br>57.87 | 4.52<br>4.61 |
| 149 | 4-Cl-C6H4-O-CH(C2H5)-CONHCH2-(2-pyridyl) | m.p. 75~77° C. | 5.62<br>5.65 | 63.05<br>63.03 | 9.19<br>9.20 |
| 150 | 2,6-Cl2-C6H3-O-CH(C2H5)-CONHCH2-(2-thienyl) | m.p. 73~75° C. | 4.39<br>4.44 | 52.33<br>52.34 | 4.07<br>4.16 |
| 151 | 2,6-Cl2-C6H3-O-CH(C2H5)-CONHCH2-(3-pyridyl) | m.p. 63~65° C. | 4.76<br>4.79 | 56.65<br>56.58 | 8.26<br>8.34 |
| 152 | 3,5-Cl2-C6H3-O-CH(C2H5)-CONHCH2-(2-furyl) | m.p. 100~101° C. | 4.61<br>4.63 | 54.89<br>54.67 | 4.27<br>4.17 |
| 153 | 3,5-Cl2-C6H3-O-CH(C2H5)-CONHCH2-(2-thienyl) | m.p. 111~113° C. | 4.39<br>4.41 | 52.33<br>52.17 | 4.07<br>3.88 |
| 154 | 3,5-Cl2-C6H3-O-CH(C2H5)-CONHCH2-(3-pyridyl) | m.p. 105~107° C. | 4.76<br>4.73 | 56.65<br>56.53 | 8.26<br>8.21 |
| 155 | 3,4-Cl2-C6H3-O-CH(C2H5)-CONHCH2-(2-furyl) | m.p. 72~74° C. | 4.61<br>4.63 | 54.89<br>54.57 | 4.27<br>4.23 |
| 156 | 3,4-Cl2-C6H3-O-CH(C2H5)-CONHCH2-(2-thienyl) | m.p. 82~84° C. | 4.39<br>4.39 | 52.33<br>52.11 | 4.07<br>4.07 |

TABLE 1-continued

| Compound No. | Chemical formula | Physicochemical properties | Elementary analysis H | C | N |
|---|---|---|---|---|---|
| 157 | 3,4-dichlorophenyl-OCH($C_2H_5$)CONHCH$_2$-(2-pyridyl) | m.p. 67~69° C. | 4.76<br>4.80 | 56.65<br>56.49 | 8.26<br>7.91 |
| 158 | 3,4-dichlorophenyl-OCH($C_2H_5$)CONHCH$_2$-(3-pyridyl) | $n_D^{26}$ 1.5736 | 4.76<br>4.77 | 56.65<br>56.67 | 8.26<br>7.92 |
| 159 | 3-nitrophenyl-OCH($C_2H_5$)CONHCH$_2$-(2-furyl) | m.p. 104~106° C. | 5.30<br>5.32 | 59.20<br>58.89 | 9.21<br>9.15 |
| 160 | 3-chlorophenyl-OCH($C_2H_5$)CONHCH$_2$-(1-naphthyl) | m.p. 108~110° C. | 5.70<br>5.80 | 71.28<br>71.09 | 3.96<br>3.97 |
| 161 | 2-methoxyphenyl-OCH($C_2H_5$)CONHCH$_2$-phenyl | m.p 70~72° C. | 7.07<br>7.21 | 72.21<br>72.45 | 4.68<br>4.67 |
| 162 | 2-methoxyphenyl-OCH($C_2H_5$)CONHCH$_2$-(2-methylphenyl) | m.p. 67~68° C. | 7.40<br>7.37 | 72.82<br>72.62 | 4.47<br>4.39 |
| 163 | 3-methoxyphenyl-OCH($C_2H_5$)CONHCH$_2$-phenyl | m.p. 63~64° C. | 7.07<br>7.08 | 72.21<br>72.10 | 4.68<br>4.75 |
| 164 | 3-methoxyphenyl-OCH($C_2H_5$)CONHCH$_2$-(2-methoxyphenyl) | $n_D^{24}$ 1.5564 | 7.04<br>7.03 | 69.28<br>69.02 | 4.25<br>4.26 |
| 165 | 4-methoxyphenyl-OCH($C_2H_5$)CONHCH$_2$-phenyl | m.p. 72~74° C. | 7.07<br>7.06 | 72.21<br>71.87 | 4.68<br>4.65 |

TABLE 1-continued

| Compound No. | Chemical formula | Physicochemical properties | Elementary analysis H | C | N |
|---|---|---|---|---|---|
| 166 | CH₃O—C₆H₄—OCH(C₂H₅)CONHCH₂—C₆H₄—CH₃ | m.p. 54~56° C. | 7.40<br>7.19 | 72.82<br>72.80 | 4.47<br>4.35 |
| 167 | C₂H₅C(O)—C₆H₃(CH₃)—OCH(C₂H₅)CONHCH₂—C₆H₅ | m.p. 86~87° C. | 7.42<br>7.38 | 74.31<br>73.98 | 4.13<br>4.09 |
| 168 | CH₃—C₆H₃(NO₂)—OCH(C₂H₅)CONHCH₂—C₆H₅ | m.p. 99~100° C. | 6.14<br>6.17 | 65.84<br>65.88 | 8.53<br>8.50 |
| 169 | C₆H₄(NO₂)—OCH(C₂H₅)CONHCH₂—C₆H₅ | m.p. 90~93° C. | 5.75<br>5.82 | 64.96<br>64.75 | 8.91<br>8.80 |
| 170 | C₆H₄(NO₂)—OCH(C₂H₅)CONHCH₂—C₆H₄—CH₃ | m.p. 67~69° C. | 6.14<br>6.16 | 65.84<br>65.46 | 8.53<br>8.52 |
| 171 | C₆H₄(NO₂)—OCH(C₂H₅)CONHCH₂—C₆H₄—OCH₃ | m.p. 73~76° C. | 5.85<br>5.89 | 62.78<br>62.71 | 8.14<br>8.14 |
| 172 | O₂N—C₆H₄—OCH(C₂H₅)CONHCH₂—C₆H₅ | m.p. 114~116° C. | 5.75<br>5.84 | 64.96<br>65.00 | 8.91<br>8.92 |
| 173 | O₂N—C₆H₄—OCH(C₂H₅)CONHCH₂—C₆H₅ | m.p. 123~125° C. | 5.75<br>5.74 | 64.96<br>64.68 | 8.91<br>8.84 |
| 174 | O₂N—C₆H₄—OCH(C₂H₅)CONHCH₂—C₆H₄—CH₃ | m.p. 135~136° C. | 6.14<br>6.20 | 65.84<br>65.74 | 8.53<br>8.53 |
| 175 | O₂N—C₆H₄—OCH(C₂H₅)CONHCH₂—C₆H₄—OCH₃ | m.p. 109~112° C. | 5.85<br>5.90 | 62.78<br>63.12 | 8.14<br>8.27 |

TABLE 1-continued

| Compound No. | Chemical formula | Physicochemical properties | Elementary analysis H | C | N |
|---|---|---|---|---|---|
| 176 | 3-NC-C₆H₄-OCH(C₂H₅)CONHCH₂-C₆H₅ | m.p. 82~85° C. | 6.16<br>6.28 | 73.45<br>73.52 | 9.52<br>9.48 |
| 177 | 3-F-C₆H₄-OCH(C₂H₅)CONHCH₂-C₆H₅ | m.p. 79~82° C. | 6.31<br>6.48 | 71.06<br>71.06 | 4.87<br>4.96 |
| 178 | 3-Cl-C₆H₄-OCH(C₂H₅)CONHCH₂-C₆H₄-4-NO₂ | m.p. 100~102° C. | 4.91<br>4.90 | 58.54<br>58.32 | 8.03<br>7.98 |
| 179 | 4-Br-C₆H₄-OCH(C₂H₅)CONHCH₂-C₆H₅ | m.p. 99~100° C. | 5.21<br>5.26 | 58.63<br>58.76 | 4.02<br>4.03 |
| 180 | 4-I-C₆H₄-OCH(C₂H₅)CONHCH₂-C₆H₅ | m.p. 110~112° C. | 4.59<br>4.64 | 51.65<br>51.66 | 3.54<br>3.59 |
| 181 | 3-CF₃-C₆H₄-OCH(C₂H₅)CONHCH₂-C₆H₅ | $n_D^{23}$ 1.5146 | 5.38<br>5.21 | 64.09<br>64.35 | 4.15<br>4.02 |
| 182 | 3-CF₃-C₆H₄-OCH(C₂H₅)CON(CH₃)CH₂-C₆H₅ | $n_D^{26}$ 1.5119 | 5.74<br>5.91 | 64.95<br>64.75 | 3.97<br>3.41 |
| 183 | 3-CF₃-C₆H₄-OCH(C₂H₅)CONHCH(CH₃)-C₆H₅ | $n_D^{23}$ 1.5121 | 5.74<br>5.34 | 64.95<br>64.28 | 3.97<br>3.85 |
| 184 | 3-CF₃-C₆H₄-OCH(C₂H₅)CONHCH(C₂H₅)-C₆H₅ | m.p. 106~109° C. | 6.07<br>6.15 | 65.74<br>65.92 | 3.83<br>3.91 |
| 185 | 3-CF₃-C₆H₄-OCH(C₂H₅)CON(C₂H₅)CH₂-C₆H₅ | $n_D^{18}$ 1.5143 | 6.07<br>6.03 | 65.74<br>65.60 | 3.83<br>3.56 |

TABLE 1-continued

| Compound No. | Chemical formula | Physicochemical properties | Elementary analysis H | C | N |
|---|---|---|---|---|---|
| 186 | 3-CF$_3$-C$_6$H$_4$-OCH(C$_2$H$_5$)CON(C$_3$H$_7$-n)(CH$_2$C$_6$H$_5$) | n$_D^{16}$ 1.5106 | 6.38 6.93 | 66.47 66.35 | 3.69 3.51 |
| 187 | 3-CF$_3$-C$_6$H$_4$-OCH(C$_2$H$_5$)CON(C$_3$H$_7$-i)(CH$_2$C$_6$H$_5$) | n$_D^{16}$ 1.5133 | 6.38 5.84 | 66.47 66.77 | 3.69 3.26 |
| 188 | 3-CF$_3$-C$_6$H$_4$-OCH(C$_2$H$_5$)CON(CH$_2$-CH=CH$_2$)(CH$_2$C$_6$H$_5$) | n$_D^{16}$ 1.5177 | 5.38 5.49 | 66.83 67.01 | 3.71 3.40 |
| 189 | 3-CF$_3$-C$_6$H$_4$-OCH(C$_2$H$_5$)CON(CH$_2$-C≡CH)(CH$_2$C$_6$H$_5$) | n$_D^{14}$ 1.5217 | 5.37 5.34 | 67.19 67.33 | 3.73 3.56 |
| 190 | 3-CF$_3$-C$_6$H$_4$-OCH(C$_2$H$_5$)CON(OCH$_3$)(CH$_2$C$_6$H$_5$) | n$_D^{25}$ 1.5094 | 5.49 5.28 | 62.12 62.09 | 3.81 3.92 |
| 191 | 3-CF$_3$-C$_6$H$_4$-OCH(C$_2$H$_5$)CONHCH$_2$-(2-CH$_3$-C$_6$H$_4$) | m.p. 85~87° C. | 5.74 5.46 | 64.95 64.63 | 3.97 3.93 |
| 192 | 3-CF$_3$-C$_6$H$_4$-OCH(C$_2$H$_5$)CONHCH$_2$-(3-CH$_3$-C$_6$H$_4$) | n$_D^{23}$ 1.5148 | 5.74 5.38 | 64.95 64.62 | 3.97 3.88 |
| 193 | 3-CF$_3$-C$_6$H$_4$-OCH(C$_2$H$_5$)CONHCH$_2$-(4-CH$_3$-C$_6$H$_4$) | m.p. 106~107° C. | 6.74 6.34 | 64.95 64.56 | 3.97 3.87 |
| 194 | 3-CF$_3$-C$_6$H$_4$-OCH(C$_2$H$_5$)CON(CH$_3$)(CH$_2$-(2-CH$_3$-C$_6$H$_4$)) | n$_D^{22}$ 1.5204 | 6.07 6.06 | 65.74 65.88 | 3.83 3.76 |

TABLE 1-continued

| Compound No. | Chemical formula | Physicochemical properties | Elementary analysis H | C | N |
|---|---|---|---|---|---|
| 195 | 3-CF$_3$-C$_6$H$_4$-O-CH(C$_2$H$_5$)-CON(C$_2$H$_5$)-CH$_2$-(2-CH$_3$-C$_6$H$_4$) | $n_D^{22}$ 1.5166 | 6.38 / 6.52 | 66.47 / 66.48 | 3.69 / 3.60 |
| 196 | 3-CF$_3$-C$_6$H$_4$-O-CH(C$_2$H$_5$)-CON(i-C$_3$H$_7$)-CH$_2$-(2-CH$_3$-C$_6$H$_4$) | $n_D^{22}$ 1.5142 | 6.66 / 6.02 | 67.16 / 66.85 | 3.56 / 3.45 |
| 197 | 3-CF$_3$-C$_6$H$_4$-O-CH(C$_2$H$_5$)-CON(CH$_2$-CH=CH$_2$)-CH$_2$-(2-CH$_3$-C$_6$H$_4$) | $n_D^{22}$ 1.5209 | 6.18 / 6.17 | 67.50 / 67.10 | 3.58 / 3.56 |
| 198 | 3-CF$_3$-C$_6$H$_4$-O-CH(C$_2$H$_5$)-CON(CH$_3$)-CH$_2$-(3-CH$_3$-C$_6$H$_4$) | $n_D^{14}$ 1.5174 | 6.07 / 6.03 | 65.74 / 65.46 | 3.83 / 3.66 |
| 199 | 3-CF$_3$-C$_6$H$_4$-O-CH(C$_2$H$_5$)-CON(C$_2$H$_5$)-CH$_2$-(3-CH$_3$-C$_6$H$_4$) | $n_D^{23}$ 1.5128 | 6.38 / 6.66 | 66.47 / 66.16 | 3.69 / 3.63 |
| 200 | 3-CF$_3$-C$_6$H$_4$-O-CH(C$_2$H$_5$)-CON(i-C$_3$H$_7$)-CH$_2$-(3-CH$_3$-C$_6$H$_4$) | $n_D^{23}$ 1.5115 | 6.66 / 6.59 | 67.16 / 66.89 | 3.56 / 3.20 |
| 201 | 3-CF$_3$-C$_6$H$_4$-O-CH(C$_2$H$_5$)-CON(CH$_2$-CH=CH$_2$)-CH$_2$-(3-CH$_3$-C$_6$H$_4$) | $n_D^{22}$ 1.5164 | 6.18 / 5.99 | 67.50 / 67.30 | 3.58 / 3.25 |
| 202 | 3-CF$_3$-C$_6$H$_4$-O-CH(C$_2$H$_5$)-CONHCH$_2$-(2-CH$_3$,4-CH$_3$-C$_6$H$_3$) | m.p. 99~101° C. | 6.07 / 6.15 | 65.74 / 65.95 | 3.83 / 3.83 |

TABLE 1-continued

| Compound No. | Chemical formula | Physicochemical properties | Elementary analysis H | C | N |
|---|---|---|---|---|---|
| 203 | 3-CF$_3$-C$_6$H$_4$-OCH(C$_2$H$_5$)CONHCH$_2$-C$_6$H$_4$-2-OCH$_3$ | n$_D^{26}$ 1.5169 | 5.13<br>5.24 | 61.18<br>61.50 | 3.96<br>3.53 |
| 204 | 3-CF$_3$-C$_6$H$_4$-OCH(C$_2$H$_5$)CONHCH$_2$-C$_6$H$_4$-3-OCH$_3$ | m.p. 63~65° C. | 5.13<br>5.08 | 61.18<br>61.38 | 3.96<br>3.71 |
| 205 | 3-CF$_3$-C$_6$H$_4$-OCH(C$_2$H$_5$)CONHCH$_2$-C$_6$H$_4$-4-OCH$_3$ | m.p. 72~73° C. | 5.13<br>5.27 | 61.18<br>61.12 | 3.96<br>3.74 |
| 206 | 3-CF$_3$-C$_6$H$_4$-OCH(C$_2$H$_5$)CON(CH$_3$)CH$_2$-C$_6$H$_4$-2-OCH$_3$ | n$_D^{16}$ 1.5217 | 5.82<br>5.94 | 62.98<br>62.77 | 3.67<br>3.41 |
| 207 | 3-CF$_3$-C$_6$H$_4$-OCH(C$_2$H$_5$)CON(C$_2$H$_5$)CH$_2$-C$_6$H$_4$-2-OCH$_3$ | n$_D^{16}$ 1.5181 | 6.12<br>6.26 | 63.78<br>63.55 | 3.57<br>3.34 |
| 208 | 3-CF$_3$-C$_6$H$_4$-OCH(C$_2$H$_5$)CONHCH$_2$-(3,4-methylenedioxyphenyl) | m.p. 72~73° C. | 4.76<br>4.36 | 59.83<br>60.10 | 3.67<br>3.75 |
| 209 | 3-CF$_3$-C$_6$H$_4$-OCH(C$_2$H$_5$)CONHCH$_2$-C$_6$H$_4$-2-Cl | m.p. 66~68° C. | 4.61<br>4.72 | 58.15<br>57.92 | 3.77<br>3.69 |
| 210 | 3-CF$_3$-C$_6$H$_4$-OCH(C$_2$H$_5$)CONHCH$_2$-C$_6$H$_4$-4-Cl | m.p. 90~92° C. | 4.61<br>4.28 | 58.15<br>57.85 | 3.77<br>3.71 |
| 211 | 3-CF$_3$-C$_6$H$_4$-OCH(C$_2$H$_5$)CON(CH$_3$)CH$_2$-C$_6$H$_4$-2-Cl | n$_D^{16}$ 1.5243 | 4.76<br>5.01 | 59.83<br>59.76 | 3.67<br>3.39 |

TABLE 1-continued
| Compound No. | Chemical formula | Physicochemical properties | Elementary analysis H | C | N |
|---|---|---|---|---|---|
| 212 | 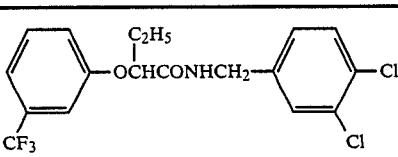 | $n_D^{20}$ 1.5274 | 3.97<br>3.89 | 53.22<br>53.15 | 3.45<br>3.22 |
| 213 | 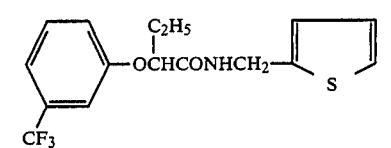 | m.p. 56~58° C. | 4.70<br>4.52 | 55.96<br>55.96 | 4.08<br>4.13 |
| 214 | 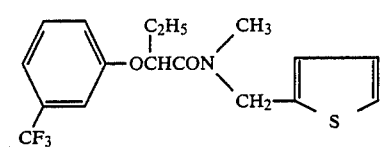 | $n_D^{14}$ 1.5225 | 5.08<br>5.05 | 57.13<br>56.92 | 3.92<br>3.69 |
| 215 | 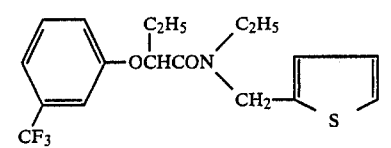 | $n_D^{14}$ 1.5212 | 5.43<br>5.45 | 58.20<br>57.96 | 3.77<br>3.60 |
| 216 | 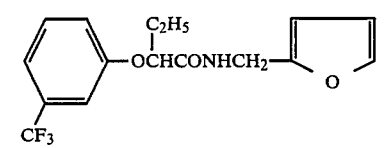 | $n_D^{26}$ 1.4930 | 4.93<br>4.76 | 58.71<br>58.81 | 4.28<br>4.05 |
| 217 | 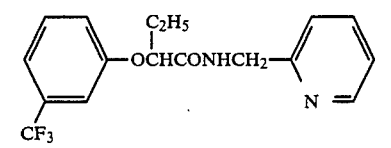 | m.p. 60~62° C. | 5.07<br>4.90 | 60.35<br>60.46 | 8.28<br>8.38 |
| 218 | 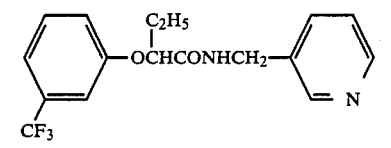 | $n_D^{23}$ 1.5148 | 5.07<br>5.04 | 60.35<br>60.17 | 8.28<br>7.69 |
| 219 | 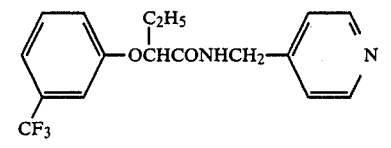 | $n_D^{23}$ 1.5121 | 5.07<br>4.83 | 60.35<br>60.15 | 8.28<br>8.03 |
| 220 | 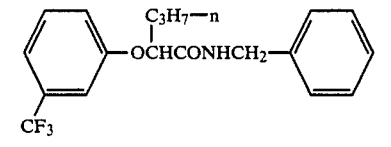 | $n_D^{24.0}$ 1.5144<br>m.p. 73~76° C. | 5.74<br>5.83 | 64.94<br>65.20 | 3.99<br>4.23 |
| 221 | 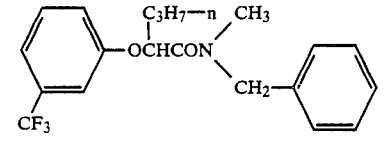 | $n_D^{11}$ 1.5162 | 6.07<br>6.07 | 65.74<br>65.09 | 3.83<br>3.79 |

TABLE 1-continued

| Compound No. | Chemical formula | Physicochemical properties | Elementary analysis H | C | N |
|---|---|---|---|---|---|
| 222 | 3-CF$_3$-C$_6$H$_4$-OCH(C$_3$H$_7$-n)CONHCH$_2$-(2-CH$_3$-C$_6$H$_4$) | m.p. 84~86° C. | 6.07 6.07 | 65.74 65.79 | 3.83 4.14 |
| 223 | 3-CF$_3$-C$_6$H$_4$-OCH(C$_3$H$_7$-n)CONHCH$_2$-(3-CH$_3$-C$_6$H$_4$) | m.p. 54~55° C. | 6.07 5.98 | 65.74 65.81 | 3.85 3.98 |
| 224 | 3-CF$_3$-C$_6$H$_4$-OCH(C$_3$H$_7$-n)CONHCH$_2$-(2-Cl-C$_6$H$_4$) | m.p. 65~67° C. | 4.96 4.95 | 59.15 58.94 | 3.63 3.81 |
| 225 | 3-CF$_3$-C$_6$H$_4$-OCH(C$_3$H$_7$-n)CONHCH$_2$-(2-pyridyl) | m.p. 56~57° C. | 5.43 5.44 | 61.35 61.83 | 7.95 8.35 |
| 226 | 4-Cl-3-CF$_3$-C$_6$H$_3$-OCH(C$_2$H$_5$)CONHCH$_2$-C$_6$H$_5$ | m.p. 93~95° C. | 4.61 4.56 | 58.14 57.94 | 3.77 3.76 |
| 227 | 4-Cl-3-CF$_3$-C$_6$H$_3$-OCH(C$_2$H$_5$)CON(CH$_3$)(CH$_2$-C$_6$H$_5$) | $n_D^{21}$ 1.5266 | 4.96 4.84 | 59.15 59.35 | 3.63 3.41 |
| 228 | 4-Cl-3-CF$_3$-C$_6$H$_3$-OCH(C$_2$H$_5$)CON(C$_2$H$_5$)(CH$_2$-C$_6$H$_5$) | $n_D^{20}$ 1.5254 | 5.29 5.23 | 60.07 59.44 | 3.50 3.51 |
| 229 | 4-Cl-3-CF$_3$-C$_6$H$_3$-OCH(C$_2$H$_5$)CON(CH$_2$-CH=CH$_2$)(CH$_2$-C$_6$H$_5$) | $n_D^{20}$ 1.5310 | 5.14 5.13 | 61.24 60.94 | 3.40 3.38 |
| 230 | 4-Cl-3-CF$_3$-C$_6$H$_3$-OCH(C$_2$H$_5$)CON(CH$_2$-C≡CH)(CH$_2$-C$_6$H$_5$) | $n_D^{19}$ 1.5320 | 4.67 4.69 | 61.54 61.18 | 3.42 3.33 |
| 231 | 4-Cl-3-CF$_3$-C$_6$H$_3$-OCH(C$_2$H$_5$)CON(C$_3$H$_7$-i)(CH$_2$-C$_6$H$_5$) | $n_D^{15.4}$ 1.5284 | 5.60 5.81 | 60.94 60.77 | 3.39 3.52 |

TABLE 1-continued

| Compound No. | Chemical formula | Physicochemical properties | Elementary analysis H | C | N |
|---|---|---|---|---|---|
| 232 | 4-Cl-3-CF$_3$-C$_6$H$_3$-OCH(C$_2$H$_5$)CONHCH$_2$-C$_6$H$_4$-2-CH$_3$ | m.p. 107~109° C. | 4.96 4.91 | 59.15 59.34 | 3.63 3.87 |
| 233 | 4-Cl-3-CF$_3$-C$_6$H$_3$-OCH(C$_2$H$_5$)CONHCH$_2$-C$_6$H$_4$-3-CH$_3$ | m.p. 97~99° C. | 4.96 4.88 | 59.15 59.23 | 3.63 3.66 |
| 234 | 4-Cl-3-CF$_3$-C$_6$H$_3$-OCH(C$_2$H$_5$)CONHCH$_2$-C$_6$H$_4$-4-CH$_3$ | m.p. 111~113° C. | 4.96 4.82 | 59.15 59.02 | 3.63 3.68 |
| 235 | 4-Cl-3-CF$_3$-C$_6$H$_3$-OCH(C$_2$H$_5$)CONHCH$_2$-C$_6$H$_4$-2-OCH$_3$ | m.p. 96~98° C. | 4.77 4.64 | 56.79 56.52 | 3.49 3.48 |
| 236 | 4-Cl-3-CF$_3$-C$_6$H$_3$-OCH(C$_2$H$_5$)CONHCH$_2$-C$_6$H$_4$-3-OCH$_3$ | m.p. 99~100° C. | 4.77 4.70 | 56.79 56.77 | 3.49 3.52 |
| 237 | 4-Cl-3-CF$_3$-C$_6$H$_3$-OCH(C$_2$H$_5$)CONHCH$_2$-C$_6$H$_4$-4-OCH$_3$ | m.p. 72~74° C. | 4.77 4.71 | 56.79 57.01 | 3.49 3.50 |
| 238 | 4-Cl-3-CF$_3$-C$_6$H$_3$-CH(C$_2$H$_5$)CON(CH$_3$)CH$_2$-C$_6$H$_4$-CH$_3$O | $n_D^{15.4}$ 1.5366 | 5.09 4.91 | 57.76 57.93 | 3.37 3.60 |
| 239 | 4-Cl-3-CF$_3$-C$_6$H$_3$-OCH(C$_2$H$_5$)CONCH$_2$-C$_6$H$_4$-Cl | m.p. 111~113° C. | 3.97 3.90 | 53.21 53.12 | 3.45 3.45 |
| 240 | 4-Cl-3-CF$_3$-C$_6$H$_3$-OCH(C$_2$H$_5$)CONHCH$_2$-C$_6$H$_4$-Cl | m.p. 104~106° C. | 3.97 3.95 | 53.21 53.50 | 3.45 3.53 |

TABLE 1-continued

| Compound No. | Chemical formula | Physicochemical properties | Elementary analysis H | C | N |
|---|---|---|---|---|---|
| 241 | 4-Cl-3-CF$_3$-C$_6$H$_3$-OCH(C$_2$H$_5$)CONHCH$_2$-C$_6$H$_4$-4-Cl | m.p. 99~101° C. | 3.97<br>3.89 | 53.21<br>53.06 | 3.45<br>3.45 |
| 242 | 3-CF$_3$-C$_6$H$_4$-OCH(C$_2$H$_5$)CON(CH$_3$)CH$_2$-C$_6$H$_4$-2-Cl | $n_D^{15.4}$ 1.5421 | 4.32<br>4.51 | 54.30<br>54.65 | 3.33<br>3.35 |
| 243 | 4-Cl-3-CF$_3$-C$_6$H$_3$-OCH(C$_2$H$_5$)CONHCH$_2$-(2-thienyl) | m.p. 89~91° C. | 4.00<br>4.04 | 50.86<br>51.00 | 3.71<br>3.74 |
| 244 | 4-Cl-3-CF$_3$-C$_6$H$_3$-OCH(C$_2$H$_5$)CONHCH$_2$-(2-furyl) | m.p. 76~78° C. | 4.18<br>4.22 | 53.12<br>53.16 | 3.87<br>3.95 |
| 245 | 4-Cl-3-CF$_3$-C$_6$H$_3$-OCH(C$_2$H$_5$)CONHCH$_2$-(2-pyridyl) | m.p. 71~73° C. | 4.33<br>4.30 | 54.77<br>55.00 | 7.52<br>7.52 |
| 246 | 4-Cl-3-CF$_3$-C$_6$H$_3$-OCH(C$_2$H$_5$)CONHCH$_2$-(3-pyridyl) | $n_D^{19}$ 1.5228 | 4.33<br>4.33 | 54.77<br>54.29 | 7.52<br>7.37 |
| 247 | 4-Cl-3-CF$_3$-C$_6$H$_3$-OCH(C$_2$H$_5$)CONHCH$_2$-(4-pyridyl) | $n_D^{19}$ 1.5228 | 4.33<br>4.34 | 54.77<br>54.87 | 7.52<br>7.47 |
| 248 | 4-Cl-3-CF$_3$-C$_6$H$_3$-OCH(n-C$_3$H$_7$)CONHCH$_2$-C$_6$H$_5$ | m.p. 72~74° C. | 4.96<br>4.96 | 59.15<br>59.00 | 3.63<br>3.96 |
| 249 | 4-Cl-3-CF$_3$-C$_6$H$_3$-OCH(n-C$_3$H$_7$)CON(CH$_3$)CH$_2$-C$_6$H$_5$ | $n_D^{11}$ 1.5290 | 5.29<br>5.20 | 60.07<br>60.27 | 3.50<br>3.45 |

TABLE 1-continued

| Compound No. | Chemical formula | Physicochemical properties | Elementary analysis H | C | N |
|---|---|---|---|---|---|
| 250 | Cl-C₆H₃(CF₃)-OCH(C₃H₇-n)CONHCH₂-(2-pyridyl) | m.p. 74~77° C. | 4.69 4.67 | 55.89 56.03 | 7.24 7.68 |
| 251 | Cl-C₆H₃(CH₃)-OCH(C₂H₅)CONHCH₂-C₆H₄-Cl | m.p. 107~109° C. | 5.44 5.47 | 61.37 60.73 | 3.98 4.19 |
| 252 | (CH₃)₂(Cl)C₆H₂-OCH(C₂H₅)CONHCH₂-C₆H₄-Cl | m.p. 120~122° C. | 5.78 5.80 | 62.30 61.94 | 3.82 3.78 |
| 253 | Cl-C₆H₃(CH₃)-OCH(C₂H₅)CONHCH₂-C₆H₄-OCH₃ | m.p. 84~86° C. | 6.38 6.15 | 65.61 65.83 | 4.03 4.15 |

The phenoxyalkylamide derivative according to this invention can be prepared by the reaction (1) or (2) illustrated below.

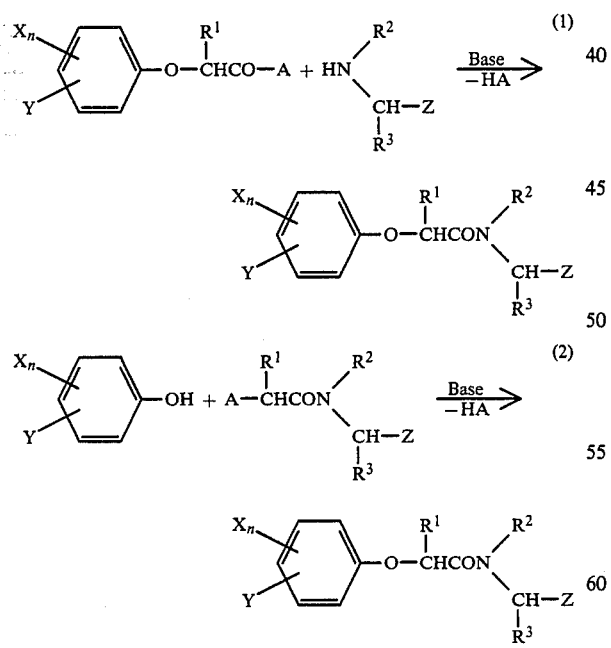

(In the above formulas (1) and (2), A represents a chlorine atom or a bromine atom; and X, n, Y, Z, R¹, R² and R³ have the same meanings as defined above.)

The above-mentioned reactions (1) and (2) may suitably be carried out by the addition of a weak base such as pyridine, triethylamine, sodium carbonate or potassium carbonate in the presence of an appropriate solvent.

As the solvent used in the reaction, there may be mentioned, for example, an aromatic hydrocarbon such as benzene, toluene and xylene; an ether such as diethyl ether, tetrahydrofuran and dioxane; and a ketone such as methyl ethyl ketone and dimethyl ketone. Particularly, in the reaction (2), an ether or a ketone may preferably be used. While the reaction temperature which depends upon the kind of the reagent and solvent used for the reaction is not critical, the reaction (1) may preferably be conducted at a temperature of 0° to 30° C., and the reaction (2), at a temperature of 50° to 130° C.

The reaction time usually is for about 1 hour to 10 hours.

Next, Examples for syntheses of the amide derivatives according to the present invention will be described below.

SYNTHESIS EXAMPLE 1.

Synthesis of N-benzyl-2-(3,5-dimethylphenoxy)-butyramide (compound of Compd. No. 30 in Table 1 shown above)

In 30 ml of benzene were dissolved 1.8 g (0.017 mole) of benzylamine and 1.2 g (0.015 mole) of pyridine, and thereto was added dropwise 3.0 g (0.013 mole) of 2-(3,5-dimethylphenoxy)-butyroyl chloride at room temperature with stirring. After the reaction was carried out for 5 hours, the reaction mixture was washed with water, dilute hydrochloric acid, dilute aqueous sodium hydroxide and then water successively. After the benzene layer was dried, the benzene was removed by distillation. The resultant crude crystals were recrystallized from n-hexane to give 2.4 g of N-benzyl-2-(3,5-dimethylphenoxy)-butyramide melting at 93°–94° C. as colorless needles.

SYNTHESIS EXAMPLE 2

Synthesis of N-(2-methylbenzyl)-2-(3,5-dichlorophenoxy)-butyramide (compound of Compd. No. 116 in Table 1 shown above)

In 30 ml of benzene were dissolved 1.5 g (0.012 mole) of 2-methylbenzylamine and 1.0 g (0.01 mole) of triethylamine, and thereto was added dropwise 2.8 g (0.01 mole) of 2-(3,5-dichlorophenoxy)-butyroyl chloride in 20 ml benzene solution at room temperature with stirring. After the reaction carried out for 2 hours, the reaction mixture was washed with dilute hydrochloric acid, dilute aqueous sodium hydroxide and then water successively. After the benzene layer was dried, the benzene was removed by distillation.

The resultant crude crystals were recrystallized from ethanol to give 2.3 g of N-(2-methylbenzyl)-2-(3,5-dichlorophenoxy)-butyramide melting at 135°~137° C. as colorless prisms.

SYNTHESIS EXAMPLE 3

Synthesis of N-benzyl-2-(4-chloro-3-methylphenoxy)-valeramide (compound of Compd. No. 54 in Table 1 shown above)

In 60 ml of acetone were dissolved 3.5 g (0.013 mole) of N-benzyl-α-bromovaleramide and 6.3 g (0.040 mole) of 4-chloro-3-methylphenol, and thereto was added 6.9 g (0.050 mole) of anhydrous potassium carbonate, and then the resultant mixture was boiled under reflux with stirring for 10 hours.

After cooling, the acetone was removed by distillation and then 100 ml of water was added to the residue. The thus precipitated oily substance was extracted with benzene.

After the benzene layer was washed with dilute hydrochloric acid, dilute aqueous sodium hydroxide and then water, and then dried, the benzene was removed by distillation. The residue was subjected to silica gel column chromatography to obtain 3.0 g of N-benzyl-2-(4-chloro-3-methylphenoxy)-valeramide as colorless oil.

The oil crystallized when allowed to stand at room temperature, and the so obtained crystals showed a melting point of 75°~78° C.

SYNTHESIS EXAMPLE 4

Synthesis of N-thienylmethyl-2-(4-chloro-3,5-dimethylphenoxy)-butyramide (compound of Compd. No. 137 in Table 1 shown above)

In 50 ml of benzene were dissolved 1.6 g (0.014 mole) of 2-aminomethylthiophene and 1.4 g (0.014 mole) of triethylamine, and thereto was added dropwise a solution of 3.1 g (0.012 mole) of 2-(4-chloro-3,5-dimethylphenoxy)-butyroyl chloride in 20 ml of benzene at room temperature with stirring. After the mixture was stirred for 1 hour and left to stand overnight, the reaction mixture was washed with water, dilute hydrochloric acid, dilute aqueous sodium hydroxide and then water successively. After the benzene layer was dried, the benzene was removed by distillation.

The resultant crude crystals were recrystallized from ethanol to give 3.0 g of N-thienylmethyl-2-(4-chloro-3,5-dimethylphenoxy)-butyramide melting at 105°~107° C. as colorless needles.

SYNTHESIS EXAMPLE 5

Synthesis of N-(2-pyridylmethyl)-2-(3-chlorophenoxy)-butyramide (compound of Compd. No. 144 in Table 1 shown above)

In 50 ml of toluene were dissolved 1.6 g (0.012 mole) of 2-aminomethylpyridine and 1.2 g (0.012 mole) of triethylamine, and thereto was added dropwise a solution 2.8 g (0.012 mole) of 2-(3-chlorophenoxy)-butyroyl chloride in 20 ml of toluene at room temperature with stirring. After the reaction was carried out for 4 hours, the reaction mixture was washed with water, dilute aqueous sodium hydroxide and then water successively. After the toluene layer was dried, the toluene was removed by distillation. The thus obtained oil was subjected to column chromatography to give 2.3 g of N-(2-pyridylmethyl)-2-(3-chlorophenoxy)-butyramide showing $n_D^{26}$ 1.5610 as pale yellow oily liquid.

SYNTHESIS EXAMPLE 6

Synthesis of N-furfuryl-2-(4-chloro-3-methylphenoxy)-butyramide (compound of Compd. No. 133 in Table 1 shown above)

In 50 ml of benzene were dissolved 1.5 g (0.015 mole) of furfurylamine and 4.0 g (0.051 mole) of pyridine, and thereto was added dropwise a solution of 3.0 g (0.012 mole) of 2-(4-chloro-3-methylphenoxy)-butyroyl chloride in 20 ml of benzene at room temperature with stirring, followed by stirring for further 5 hours. Subsequently, after the same procedure as in Synthesis Example 4 and 5 was followed, the resultant crude crystals were recrystallized from ethanol to give 1.0 g of N-furfuryl-2-(4-chloro-3-methylphenoxy)-butyramide melting at 100°~102° C. as pale brown needles.

SYNTHESIS EXAMPLE 7

Synthesis of N-benzyl-2-(3-methoxyphenoxy)-butyramide (compound of Compd. No. 163 in Table 1 shown above)

In 50 ml of toluene were dissolved 1.7 g (0.013 mole) of benzylamine and 1.0 g (0.013 mole) of pyridine, and thereto was added dropwise a solution of 2.9 g (0.013 mole) of 2-(3-methoxyphenyl)-butyroyl chloride in 20 ml of toluene at room temperature with stirring.

After the reaction was carried out for 1 hour and the reaction mixture was left to stand overnight, it was washed with water, dilute hydrochloric acid, dilute aqueous sodium hydroxide and then water successively. After the toluene layer was dried, the toluene was removed by distillation. The resultant crude crystals were recrystallized from ethanol to give 1.6 g of N-benzyl-2-(3-methoxyphenoxy)-butyramide melting at 63°~64° C. as colorless needles.

SYNTHESIS EXAMPLE 8

Synthesis of N-benzyl-2-(3-nitrophenoxy)-butyramide (compound of Compd. No. 172 in Table 1 shown above)

In 30 ml of toluene were dissolved 1.6 g (0.015 mole) of benzylamine and 1.2 g (0.015 mole) of pyridine, and thereto was added dropwise a solution of 3.1 g (0.013 mole) of 2-(3-nitrophenoxy)-butyroyl chloride in 30 ml of toluene at room temperature with stirring. Subsequently, after the same procedure as in Synthesis Example 7 was followed, the resultant crude crystals were recrystallized from ethanol to give 2.4 g of N-benzyl-2-(3-nitrophenoxy)-butyramide melting at 114°~116° C. as pale yellow needles.

SYNTHESIS EXAMPLE 9

Synthesis of N-(2-methoxybenzyl)-2-(4-nitrophenoxy)-butyramide (compound of Compd. No. 175 in Table 1 shown above)

In 50 ml of toluene were dissolved 1.9 g (0.014 mole) of 2-methoxybenzylamine and 1.2 g (0.015 mole) of pyridine. Then, was added dropwise thereto a solution of 2.8 g (0.012 mole) of 2-(4-nitrophenoxy)-butyroyl chloride in 30 ml of toluene and the mixture was treated according to the same procedure as in Synthesis Example 7. The resultant crude crystals were recrystallized from ethanol to give 2.4 g of N-(2-methoxybenzyl)-2-(4-nitrophenoxy)-butyramide melting at 109°~112° C. as colorless needles.

SYNTHESIS EXAMPLE 10

Synthesis of N-(2-chlorobenzyl)-2-(3-trifluoromethylphenoxy)-butyramide (compound of Compd. No. 209 in Table 1 shown above)

In 50 ml of toluene were dissolved 1.6 g (0.011 mole) of 2-chlorobenzylamine and 1.0 g (0.013 mole) of pyridine, and thereto was added dropwise a solution of 2.5 g (0.009 mole) of 2-(3-trifluoromethylphenoxy)-butyroyl chloride in 20 ml of toluene at room temperature with stirring. After the mixture was stirred for 1 hour and left to stand overnight, the reaction mixture was washed with water, dilute hydrochloric acid, dilute aqueous sodium hydroxide and then water successively. After the toluene layer was dried, the toluene was removed by distillation.

The resultant crude crystals were recrystallized from ethanol to give 1.7 g of N-(2-chlorobenzyl)-2-(3-trifluoromethylphenoxy)-butyramide melting at 66°~68° C. as colorless needles.

SYNTHESIS EXAMPLE 11

Synthesis of N-benzyl-2-(4-chloro-3-trifluoromethylphenoxy)-butyramide (compound of Compd. No. 226 in Table 1 shown above)

In 50 ml of toluene were dissolved 1.6 g (0.015 mole) of benzylamine and 2.4 g (0.030 mole) of pyridine. Then, was added dropwise thereto a solution of 3.0 g (0.010 mole) of 2-(4-chloro-3-trifluoromethylphenoxy)-butyroyl chloride in 30 ml of toluene and the mixture was treated, according to the same procedure as in Synthesis Example 10. The resultant crude crystals were recrystallized from ethanol to give 1.6 g of N-benzyl-2-(4-chloro-3-trifluoromethylphenoxy)-butyramide melting at 93°-95° C. as colorless needless.

SYNTHESIS EXAMPLE 12

Synthesis of N-(4-pyridylmethyl)-2-(4-chloro-3-trifluoromethylphenoxy)-butyramide (compound of Compd. No. 247 in Table 1 shown above)

In 50 ml of toluene were dissolved 1.3 g (0.012 mole) of 4-(aminomethyl)pyridine and 1.0 g (0.010 mole) of triethylamine. Thereto was added dropwise a solution of 3.0 g (0.010 mole) of 2-(4-chloro-3-trifluoromethylphenoxy)-butyroyl chloride in 30 ml of toluene at room temperature with stirring, and the mixture was treated according to the same procedure as in Synthesis Example 10. The resultant oily substance was subjected to silica gel column chromatography by eluting with toluene to obtain 1.6 g of N-(4-pyridylmethyl)-2-(4-chloro-3-trifluoromethylphenoxy)-butyramide showing $n_D^{19}$ 1.5228 as pale yellow oil.

SYNTHESIS EXAMPLE 13

Synthesis of N-benzyl-2-(4-chloro-3-methylphenoxy)-butyramide (compound of Compd. No. 49 in Table 1 shown above)

In 30 ml of toluene were dissolved 1.5 g (0.014 mole) of benzylamine and 1.4 g (0.014 mole) of triethylamine, and thereto was added dropwise a solution of 3.0 g (0.013 mole) of 2-(4-chloro-3-methylphenoxy)-butyroyl chloride in 20 ml of toluene at room temperature with stirring. After the mixture was stirred for 3 hours, the reaction mixture was washed with dilute hydrochloric acid, dilute aqueous sodium hydroxide and then water successively. After the toluene layer was dried, the toluene was removed by distillation.

The resultant crude crystals were recrystallized from ethanol to give 2.7 g of N-benzyl-2-(4-chloro-3-methylphenoxy)-butyramide melting at 95°-97° C. as colorless needles.

SYNTHESIS EXAMPLE 14

Synthesis of N-(2-chlorobenzyl)-2-(4-chloro-3-methylphenoxy)-butyramide (compound of Compd. No. 251 in Table 1 shown above)

In 50 ml of acetone were dissolved 2.5 g (0.009 mole) of N-(2-chlorobenzyl)-α-bromobutyramide and 1.3 g (0.010 mole) of 4-chloro-3-methylphenol, and thereto was added 1.5 g (0.011 mole) of anhydrous potassium carbonate and the mixture was boiled and refluxed for 8 hours with stirring. After cooling, the acetone was removed by distillation. To residue was added 80 ml of water, and precipitates were extracted with toluene. After the toluene layer was washed with dilute aqueous sodium hydroxide and water successively and then was dehydrated by aqueous sodium sulfate, the toluene was removed by distillation.

The resultant crude crystals were recrystallized from ethanol to give 1.7 g of N-(2-chlorobenzyl)-2-(4-chloro-3-methylphenoxy)-butyramide melting at 107°-109° C. as colorless needles.

According to this invention, there is provided a herbicidal composition which comprises as an active ingredient the phenoxyalkylamide derivative of the above formula (I) and an agriculturally acceptable carrier and method of use of the same.

When the phenoxyalkylamide derivative according to the present invention is to be applied as a herbicide, the derivative may be formulated for use to the preparations of any form commonly employed as a herbicide, for example, dusts, granules, wettable powders, emulsifiable concentrates, water soluble powders, liquid formulations, aerosols, fumigants and so on, with admixture of such an inert carrier as solid carrier, liquid carrier and emulsifying dispersant and, if required, other auxiliary agents.

As the inert carrier, there may be mentioned any of solid, liquid or gaseous carriers oridinarily employed in the art for herbicides and, for example, talc, clay, kaolin, diatomaceous earth, calcium carbonate, potassium chlorate, saltpeter, wood powder, white carbon, nitrocellulose, starch, benzene, xylene, n-hexane, gum arabic, vinyl chloride, carbon dioxide, fleon, propane, butane, bentonite, methylnaphthalene, cyclohexanone, isophoron and the like.

The herbicidal composition of this invention may also optionally be blended with any auxiliary agents for preparation, for example, spreaders, diluents, surface active agents, solvents and the like as usually done in the art.

Moreover, the herbicidal composition of this invention may also be admixed with other herbicides, fungicides, insecticides, other agricultural chemicals, fertilizers, e.g. urea, ammonium sulfate, ammonium phosphate, potassic fertilizers, soil conditioners and the like.

As the herbicides which may advantageously be admixed with the compound of formula (I), there may be mentioned a thiocarbamate type herbicide such as Benthiocarb (Saturn), Molinate (Ordram), etc.; an acid amide type herbicide such as Alachlor (Rasso), Butachlor (Machete), etc.; a phenoxy type herbicide such as 2,4-PA, MCP, etc.; a diphenyl ether type herbicide such as Nitrofen (NIP), Chlornitrofen (MO), etc.; a urea type herbicide such as Diuron (Karmex D), Linuron (Afalon), etc.; a triazine type herbicide such as Simazin (Prinsep), Afrazin (Gasaprim), etc.; and other herbicides such as Trifluorolin (Treflan), Oxadiazon (Ronstar), ACN (Mogeton), Bentaron (Basagran), etc.

The above-mentioned carriers and various auxiliary agents may be optionally utilized alone or in combination therewith for desired purposes.

In general, the herbicidal composition of this invention may contain the phenoxyalkylamide derivative in an amount of 0.1~90% by weight, based upon the finished composition and the content of the active derivative in a herbicidal composition may usually depend upon the preparation form to be formulated, for instance, ordinarily 0.1~50 parts by weight for dusts, 0.1~70 parts by weight for wettable powders, 0.1~50 parts by weight for granules, 0.1~70 parts by weight for emulsifiable concentrates and the like.

While the amount of the herbicidal composition to be applied to a field is defferent depending upon the method of use, the place for use and a kind of object weeds, it usually is 0.5~100 g/are, preferably 1~50 g/are with respect to the active ingredient, i.e. the amide derivative of this invention.

Further, in the present invention, the herbicidal composition could be applied for a paddy field. In this case, the herbicidal composition may preferably comprise a mixture of a benzylamide derivative of a phenoxyalkanoic acid represented by the following formula (III):

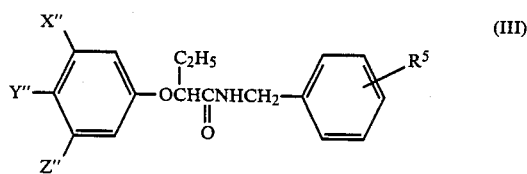

wherein X" represents a methyl group or a hydrogen atom, Y" represents a halogen atom or a hydrogen atom, Z" represents a methyl group, a halogen atom or a trifluoromethyl group, and $R^5$ represents a methyl group, a methoxy group, a halogen atom or a hydrogen atom, with 1-(α,α-dimethylbenzyl)-3-(4-methylphenyl-)urea which alleviates markedly the whitening phenomenon of paddy rice, as clearly be seen from the results of test examples as shown below, has very high selectivity between various weeds and crops, and is very excellent as a herbicidal composition for paddy field.

The herbicidal composition for paddy field in this invention has very high herbicidal activities against a broad scope of various weeds occurring in paddy field, including barnyard grass, annual broad leaf weeds, slender spikerush (Elecharis acicularis L. var. *Longesta Stevenson*), *Scipus hotarui Ohwi* and the like. Moreover, it has substantially no deleterious effect of agricultural chemical on paddy rice even when applied for harvesting of paddy rice under the bad environment as described above. Further, it is also free from toxicity to humans, animals, fishes and shellfishes and has also no objectionable odor. Accordingly, the herbicidal composition of this invention can be applied at any stage of cultivation of paddy rice, including, of course, the stages before and after transplanting of rice seedlings in cultivation by setting seedlings, as well as the stages before and after seeding of paddy rice in cultivation by direct seeding, and also stages during young seedlings and medium seedlings, without affecting growth of paddy rice at all.

The other effective ingredient in the herbicidal composition in this invention, 1-(α,α-dimethylbenzyl)-3-(4-methylphenyl)urea, is a known herbicidal component generally called as dymrone, sold under the trade name of Shoron. In the present specification, 1-(α,α-dimethylbenzyl)-3-(4-methylphenyl)urea is hereinafter called as dymrone.

Dymrone is a herbicide, having a specific selectivity, which exhibits excellent herbicidal activity against Slender spikerush (Eleocharis acicularis L. var *Longiseta Sevenson*) and *Scipus hotarui Ohwi* but has substantially no herbicidal activity against other weeds. Accordingly, dymrone is provided for use by mixing with another chemical having low herbicidal activity against Slender spikerush (Eleocharis acicularis L. var *Longiseta Sevenson*) and *Scipus hotarui Ohwi* in the form to supplement its effect, namely as a mixing agent with another chemical. However, there has been no example in the prior art in which another chemical is mixed with dymrone for the purpose of preventing whitening phenomenon of paddy rice in such a chemical, as practiced in the present invention. Such a potential ability of dymrone has been entirely unexpected in the prior art.

In this invention, dymrone is used in an amount of 0.1 to 5 parts by weight, preferably 0.5 to 2 parts by weight based on 1 part by weight of the benzylamide derivative of phenoxyalkanoic acid (III).

Further, the herbicidal composition for paddy field of this invention can be used as a suitable mixture with other chemicals, including, of course, known herbicides such as the general name pyrazolate (trade name: Sanbard) or the general name naproanililde (trade name: Uribest), antimicrobial agents, pesticides and other agricultural chemicals, urea, ammonium sulfate, ammonium phosphate, potassium salts and other fertilizers, soil improving agents, etc. By mixing of these third components, the action of dymrone to prevent the chemical damage of leaf sheaf whitening will not be alleviated at all.

The herbicidal composition for paddy field in this invention may be used in an amount, which may slightly differ depending on the manner of use, the place where it is applied or the kind of the weed to be controlled, but generally in an amount of 0.5 to 100 g/are, preferably 1 to 50 g/are, of the effective ingredients, namely the benzylamide derivative of the phenoxyalkanoic acid and dymrone.

Next, Examples of the preparation of the present herbicidal composition are given below. All parts are given by weight hereinafter unless otherwise stated.

HERBICIDAL COMPOSITION 1 50 parts of N-benzyl-2-(3,5-dimethylphenoxy)-butyramide (compound of Compd. No. 30), 40 parts of xylene and 10 parts of SORPOL 800 (trade name: surface active agent) were homogeneously blended and dissolved to obtain an emulsifiable concentrate.

HERBICIDAL COMPOSITION 2 50 parts of N-(2-methylbenzyl)-2-(3,5-dichlorophenoxy)butyramide (compound of Compd. No. 116), 30 parts of kaolin, 15 parts of bentonite and 5 parts of sodium lignosulfonate were homogeneously blended and pulverized to obtain a wettable powder.

HERBICIDAL COMPOSITION 3

7 parts of N-benzyl-2-(3-chlorophenoxy)-butyramide (compound of Compd. No. 67), 60 parts of bentonite, 30 parts of talc and 3 parts of sodium naphthalenesulfonate were homogeneously blended and pulverized. To the blend was added a small amount of water and the mixture was kneaded, granulated by using a granulating machine and dried to give granules.

HERBICIDAL COMPOSITION 4

50 parts of N-thienylmethyl-2-(3,4-dichlorophenoxy)-butyramide (compound of Compd. No. 156), 40 parts of xylene and SORPOL 800 (trade name: surface active agent) were homogeneously blended and dissolved to obtain an emulsifiable concentrate.

HERBICIDAL COMPOSITION 5

50 parts of N-(2-pyridylmethyl)-2-(4-chloro-3,5-dimethylphenoxy)-butyramide (compound of Compd. No. 138), 30 parts of kaolin, 15 parts of bentonite and 5 parts of sodium lignosulfonate were homogeneously blended and pulverized to obtain a wettable powder.

HERBICIDAL COMPOSITION 6

7 parts of N-furfuryl-2-(4-chloro-3-methylphenoxy)-butyramide (compound of Compd. No. 133), 60 parts of bentonite, 30 parts of talc and 3 parts of sodium naphthalenesulfonate were homogeneously blended and pulverized. To the blend was added a small amount of water and the mixture was kneaded, granulated by using a granulating machine and dried to give granules.

HERBICIDAL COMPOSITION 7

50 parts of N-benzyl-2-(3-methoxyphenoxy)-butyramide (compound of Compd. No. 163), 40 parts of xylene and 10 parts of SORPOL 800 (trade name: surface active agent) were homogeneously blended and dissolved to obtain an emulsifiable concentrate.

HERBICIDAL COMPOSITION 8

50 parts of N-benzyl-2-(3-nitrophenoxy)-butyramide (compound of Compd. No. 172), 30 parts of kaolin, 15 parts of bentonite and 5 parts of sodium lignosulfonate were homogeneously blended and pulverized to give a wettable powder.

HERBICIDAL COMPOSITION 9

7 parts of N-benzyl-2-(4-methyl-3-nitrophenoxy)-butyramide (compound of Compd. No. 168), 60 parts of bentonite, 30 parts of talc and 3 parts of sodium naphthalnesulfonate were homogeneously blended and pulverized. To the blend was added a small amount of water and the mixture was kneaded, granulated by using a granulating machine and dried to give granules.

HERBICIDAL COMPOSITION 10

50 parts of N-benzyl-2-(3-trifluoromethylphenoxy)-butyramide (compound of Compd. No. 181), 40 parts of xylene and 10 parts of SORPOL 800 (trade name: surface active agent) were homogeneously blended and dissolved to obtain an emulsifiable concentrate.

HERBICIDAL COMPOSITION 11

50 parts of N-benzyl-2-(4-chloro-3-trifluoromethylphenoxy)-butyramide (compound of Compd. No. 226), 30 parts of kaolin, 15 parts of bentonite and 5 parts of sodium lignosulfonate were homogeneously blended and pulverized to obtain a wettable powder.

HERBICIDAL COMPOSITION 12

7 parts of N-furfuryl-2-(4-chloro-3-trifluoromethylphenoxy)-butyramide (compound of Compd. No. 244), 60 parts of bentonite, 30 parts of talc and 3 parts of sodium naphthalenesulfonate were homogeneously blended and pulverized. To the blend was added a small amount of water and the mixture was kneaded, granulated by using of a granulating machine and dried to give granules.

HERBICIDAL COMPOSITION 13

6 parts of N-benzyl-2-(3,4-dichlorophenoxy)-butyramide (compound of Compd. No. 99), 7 parts of dymrone, 30 parts of bentonite, 54 parts of talc, 1 part of Neoperex powder (trade name: available from Kao Atlas K.K.) and 2 parts of sodium lignosulfonate were homogeneously blended and pulverised. To the blend was added a small amount of water and the mixture was kneaded, granulated by using a granulating machine and dried to give granules.

HERBICIDAL COMPOSITION 14

4 parts of N-benzyl-2-(3,5-dimethylphenoxy)-butyramide (compound of Compd. No. 30), 7 parts of dymrone, 7 parts of 4-(2,4-dichlorobenzoyl)-1,3-dimethylpyrazol-5-yl-p-toluenesulfonate, 30 parts of bentonite, 49 parts of talc, 1 part of Neoperex powder (trade name: available from Kao Atlas K.K.) and 2 parts of sodium lignosulfonate were homogeneously blended and pulverised. To the blend was added a small amount of water and the mixture was kneaded, granulated by using a granulating machine and dried to give granules.

HERBICIDAL COMPOSITION 15

7 parts of N-(2-chlorobenzyl)-2-(3-trifluoromethylphenoxy)-butyramide (compound of Compd. No. 209), 7 parts of dymrone, 7 parts of α-(2-naphthoxy)-propioneanilide, 30 parts of bentonite, 46 parts of talc, 1 part of Neoperex powder (trade name: available from Kao Atlas K.K.) and 2 parts of sodium lignosulfonate were homogeneously blended and pulverised. To the blend was added a small amount of water and the mixture was kneaded, granulated by using a granulating machine and dried to give granules.

HERBICIDAL COMPOSITION 16 40 parts of N-benzyl-2-(4-chloro-3-methylphenoxy)-butyramide (compound of Compd. No. 49), 20 parts of dymrone, 38 parts of Kaolin and 2 parts of Neoperex powder (trade name: available from Kao Atlas K.K.) were homogeneously blended and pulverised to obtain a wettable powder.

The herbicidal composition of this invention exhibits excellent herbicidal effect against not only broad leaved weeds but also other weeds by the chlorosis action, and it shows little phytotoxicity against rice plants and others due to the auxin action which is observed in conventional phenoxy series herbicidal compositions known to the art. Moreover, the herbicidal composition of this invention has no toxicity against man, beast, fishes and shellfishes and no bad smell at all.

Next, the effects of the herbicidal composition according to the present invention will be explained concretely by way of Experiments shown below. The number of each test compound in each Experiment is the same as that in Table 1 shown above.

EXPERIMENT 1

Soil treatment tests for paddy field weed

Pots, each having an area of 1/9000 are, were packed with paddy soil (diluvial soil) and planted with uniformly mixed seeds of barnyardgrass (*Echinochloa crusgalli*), of broad leaved weeds (*Rotla indica* Koekne, *Lindernia Pyxidaria* L., *Monochoria vaginalis*), of *Scripus hotarui* Ohwi. and of *Cyperus difformis* L. upon the surface layer, and tuber of *Sagittaria pygmaea* Miq. or *Cyperus serotinus* Rottb. and rice plant seedlings at 1.8~3 leaf stage were also transplanted. Then, the pots were filled with water to a depth of 2~3 cm.

Then, 3 days later, i.e., at the initial stage of generation of each weed, a predetermined amount of dilute solution of a wettable powder of each test compound, which had been prepared in the same manner as in Herbicidal composition 2 above, was uniformly spread to the surface of filled water.

Four weeks after the treatment, the herbicidal effects of each test compound were investigated.

The results are shown in Table 2 wherein the herbicidal effects are evaluated according to the rating system as defined below:

5=All killed;
4=Severely damaged;
3=Moderately damaged;
2=Slightly damaged;
1=Minor damaged;
0=None (normal development)

The data on the upper and lower lines in each column of Table 2 are the results which were obtained by carrying out the experiments at concentrations of an active ingredient of 50 g/are and 25 g/are, respectively (with regard to compounds of Compd. Nos. 1 to 180), and at concentrations of an active ingredient of 25 g/are and 12.5 g/are, respectively (with regard to compounds of Compd. Nos. 181 to 253).

TABLE 2

| Compound No. | Phytotoxicity against rice plant | Herbicidal effects | | | | |
|---|---|---|---|---|---|---|
| | | barnyardgrass | broad leavedweeds | *S. hotarui* Ohwi. | *C. difformis* L. | *S. pygmaea* Miq. |
| 1 | 1 | 5 | 5 | 5 | 5 | 3 |
| | 0 | 5 | 5 | 3 | 5 | 2 |
| 2 | 0 | 5 | 5 | 5 | 5 | 2 |
| | 0 | 4 | 5 | 5 | 5 | 1 |
| 3 | 0 | 5 | 5 | 5 | 5 | 2 |
| | 0 | 5 | 5 | 5 | 5 | 2 |
| 4 | 0 | 5 | 5 | 5 | 5 | 5 |
| | 0 | 5 | 5 | 3 | 5 | 3 |
| 5 | 0 | 5 | 5 | 5 | 5 | 3 |
| | 0 | 5 | 5 | 3 | 5 | 1 |
| 6 | 0 | 3 | 5 | 5 | 4 | 2 |
| | 0 | 1 | 5 | 2 | 3 | 1 |
| 7 | 0 | 5 | 5 | 5 | 5 | 2 |
| | 0 | 4 | 5 | 4 | 5 | 1 |
| 8 | 0 | 5 | 5 | 5 | 5 | 4 |
| | 0 | 5 | 5 | 5 | 5 | 2 |
| 9 | 0 | 5 | 5 | 5 | 5 | 5 |
| | 0 | 4 | 5 | 4 | 5 | 3 |
| 10 | 0 | 5 | 5 | 5 | 5 | 3 |
| | 0 | 5 | 5 | 5 | 5 | 2 |
| 11 | 1 | 5 | 5 | 5 | 5 | 2 |
| | 0 | 4 | 5 | 5 | 5 | 1 |
| 12 | 0 | 5 | 5 | 5 | 5 | 2 |
| | 0 | 4 | 5 | 4 | 5 | 2 |
| 13 | 0 | 5 | 5 | 5 | 5 | 2 |
| | 0 | 3 | 5 | 4 | 4 | 2 |
| 14 | 0 | 5 | 5 | 5 | 5 | 3 |
| | 0 | 3 | 5 | 4 | 5 | 1 |
| 15 | 0 | 4 | 5 | 4 | 4 | 2 |
| | 0 | 2 | 5 | 3 | 2 | 1 |
| 16 | 0 | 5 | 5 | 5 | 5 | 5 |
| | 0 | 5 | 5 | 5 | 5 | 3 |
| 17 | 0 | 5 | 5 | 5 | 5 | 3 |
| | 0 | 3 | 5 | 4 | 5 | 2 |
| 18 | 0 | 5 | 5 | 4 | 5 | 2 |
| | 0 | 5 | 5 | 3 | 5 | 2 |
| 19 | 0 | 5 | 5 | 4 | 5 | 4 |
| | 0 | 4 | 5 | 4 | 4 | 2 |

TABLE 2-continued

| | | | | | | |
|---|---|---|---|---|---|---|
| 20 | 0 | 5 | 5 | 4 | 5 | 3 |
| | 0 | 3 | 5 | 3 | 4 | 2 |
| 21 | 0 | 4 | 5 | 4 | 5 | 2 |
| | 0 | 3 | 2 | 3 | 3 | 2 |
| 22 | 0 | 4 | 4 | 4 | 5 | 1 |
| | 0 | 2 | 2 | 2 | 3 | 1 |
| 23 | 0 | 5 | 5 | 4 | 5 | 2 |
| | 0 | 4 | 5 | 3 | 5 | 2 |
| 24 | 0 | 5 | 5 | 4 | 5 | 2 |
| | 0 | 4 | 5 | 3 | 5 | 2 |
| 25 | 0 | 5 | 5 | 3 | 4 | 2 |
| | 0 | 3 | 5 | 3 | 3 | 1 |
| 26 | 0 | 5 | 5 | 4 | 4 | 2 |
| | 0 | 4 | 5 | 3 | 4 | 0 |
| 27 | 0 | 5 | 5 | 5 | 5 | 4 |
| | 0 | 5 | 5 | 5 | 5 | 2 |
| 28 | 0 | 5 | 5 | 5 | 5 | 3 |
| | 0 | 3 | 5 | 4 | 5 | 1 |
| 29 | 0 | 5 | 5 | 5 | 5 | 3 |
| | 0 | 3 | 5 | 3 | 5 | 1 |
| 30 | 0 | 5 | 5 | 5 | 5 | 3 |
| | 0 | 5 | 5 | 5 | 5 | 2 |
| 31 | 0 | 5 | 5 | 5 | 5 | 5 |
| | 0 | 5 | 5 | 5 | 5 | 3 |
| 32 | 0 | 5 | 5 | 5 | 5 | 5 |
| | 0 | 5 | 5 | 3 | 5 | 2 |
| 33 | 0 | 5 | 5 | 5 | 5 | 5 |
| | 0 | 4 | 5 | 3 | 5 | 2 |
| 34 | 0 | 5 | 5 | 4 | 5 | 3 |
| | 0 | 4 | 4 | 2 | 5 | 2 |
| 35 | 0 | 5 | 5 | 4 | 5 | 2 |
| | 0 | 4 | 5 | 3 | 3 | 1 |
| 36 | 0 | 5 | 5 | 3 | 5 | 2 |
| | 0 | 5 | 5 | 2 | 4 | 2 |
| 37 | 0 | 4 | 5 | 4 | 5 | 3 |
| | 0 | 2 | 4 | 2 | 3 | 1 |
| 38 | 0 | 4 | 5 | 4 | 4 | 2 |
| | 0 | 3 | 2 | 1 | 3 | 2 |
| 39 | 0 | 4 | 5 | 4 | 5 | 3 |
| | 0 | 2 | 5 | 2 | 5 | 1 |
| 40 | 0 | 4 | 5 | 4 | 5 | 2 |
| | 0 | 2 | 5 | 3 | 5 | 2 |
| 41 | 0 | 5 | 5 | 5 | 5 | 4 |
| | 0 | 3 | 5 | 4 | 5 | 2 |
| 42 | 0 | 5 | 5 | 4 | 5 | 3 |
| | 0 | 3 | 5 | 3 | 4 | 2 |
| 43 | 0 | 5 | 5 | 4 | 4 | 2 |
| | 0 | 3 | 5 | 3 | 3 | 2 |
| 44 | 0 | 4 | 5 | 4 | 4 | 2 |
| | 0 | 3 | 5 | 2 | 2 | 2 |
| 45 | 0 | 4 | 5 | 4 | 5 | 2 |
| | 0 | 3 | 4 | 2 | 2 | 1 |
| 46 | 2 | 5 | 5 | 5 | 5 | 5 |
| | 1 | 4 | 5 | 5 | 5 | 5 |
| 47 | 0 | 5 | 5 | 5 | 5 | 5 |
| | 0 | 5 | 5 | 5 | 5 | 5 |
| 48 | 0 | 5 | 5 | 5 | 5 | 5 |
| | 0 | 5 | 5 | 5 | 5 | 5 |
| 49 | 0 | 5 | 5 | 5 | 5 | 5 |
| | 0 | 5 | 5 | 5 | 5 | 5 |
| 50 | 0 | 5 | 5 | 5 | 5 | 5 |
| | 0 | 5 | 5 | 5 | 5 | 5 |
| 51 | 0 | 5 | 5 | 5 | 5 | 5 |
| | 0 | 5 | 5 | 5 | 5 | 3 |
| 52 | 0 | 5 | 5 | 5 | 5 | 4 |
| | 0 | 5 | 5 | 4 | 5 | 2 |
| 53 | 0 | 4 | 5 | 4 | 5 | 2 |
| | 0 | 2 | 4 | 3 | 4 | 1 |
| 54 | 0 | 5 | 5 | 5 | 5 | 5 |
| | 0 | 5 | 5 | 5 | 5 | 4 |
| 55 | 0 | 5 | 5 | 5 | 5 | 5 |
| | 0 | 5 | 5 | 5 | 5 | 5 |
| 56 | 0 | 5 | 5 | 5 | 5 | 5 |
| | 0 | 5 | 5 | 5 | 5 | 5 |
| 57 | 0 | 4 | 5 | 4 | 4 | 2 |
| | 0 | 2 | 5 | 3 | 3 | 2 |
| 58 | 0 | 5 | 5 | 5 | 5 | 4 |
| | 0 | 5 | 5 | 4 | 5 | 4 |
| 59 | 0 | 4 | 5 | 4 | 4 | 2 |
| | 0 | 3 | 5 | 4 | 3 | 1 |
| 60 | 0 | 5 | 5 | 5 | 5 | 4 |
| | 0 | 5 | 5 | 4 | 5 | 2 |

TABLE 2-continued

| | | | | | | |
|---|---|---|---|---|---|---|
| 61 | 0 | 5 | 5 | 5 | 5 | 4 |
| | 0 | 3 | 5 | 4 | 5 | 3 |
| 62 | 0 | 5 | 5 | 5 | 5 | 5 |
| | 0 | 5 | 5 | 5 | 5 | 4 |
| 63 | 0 | 5 | 5 | 5 | 5 | 5 |
| | 0 | 5 | 5 | 4 | 5 | 3 |
| 64 | 0 | 5 | 5 | 5 | 5 | 3 |
| | 0 | 4 | 4 | 3 | 4 | 2 |
| 65 | 0 | 4 | 5 | 5 | 4 | 2 |
| | 0 | 2 | 4 | 5 | 2 | 2 |
| 66 | 0 | 4 | 5 | 4 | 4 | 3 |
| | 0 | 2 | 4 | 3 | 4 | 2 |
| 67 | 0 | 5 | 5 | 5 | 5 | 5 |
| | 0 | 5 | 5 | 5 | 5 | 4 |
| 68 | 1 | 5 | 5 | 5 | 5 | 5 |
| | 0 | 5 | 5 | 5 | 5 | 3 |
| 69 | 0 | 5 | 5 | 5 | 5 | 4 |
| | 0 | 4 | 5 | 4 | 5 | 3 |
| 70 | 0 | 5 | 5 | 5 | 5 | 3 |
| | 0 | 5 | 5 | 5 | 5 | 3 |
| 71 | 0 | 5 | 5 | 5 | 5 | 3 |
| | 0 | 5 | 5 | 5 | 5 | 3 |
| 72 | 0 | 5 | 5 | 4 | 5 | 3 |
| | 0 | 5 | 5 | 3 | 5 | 2 |
| 73 | 0 | 5 | 5 | 5 | 5 | 3 |
| | 0 | 5 | 5 | 5 | 5 | 2 |
| 74 | 0 | 5 | 5 | 5 | 5 | 2 |
| | 0 | 4 | 5 | 4 | 4 | 2 |
| 75 | 0 | 5 | 5 | 5 | 5 | 2 |
| | 0 | 4 | 5 | 4 | 5 | 2 |
| 76 | 0 | 4 | 5 | 5 | 5 | 2 |
| | 0 | 3 | 5 | 3 | 4 | 1 |
| 77 | 0 | 5 | 5 | 5 | 5 | 4 |
| | 0 | 5 | 5 | 5 | 5 | 1 |
| 78 | 0 | 5 | 5 | 5 | 5 | 3 |
| | 0 | 5 | 5 | 5 | 5 | 2 |
| 79 | 0 | 5 | 5 | 5 | 5 | 3 |
| | 0 | 5 | 5 | 4 | 5 | 2 |
| 80 | 0 | 5 | 5 | 4 | 5 | 5 |
| | 0 | 4 | 5 | 3 | 5 | 3 |
| 81 | 0 | 5 | 5 | 4 | 5 | 4 |
| | 0 | 4 | 5 | 2 | 4 | 2 |
| 82 | 0 | 5 | 5 | 5 | 5 | 3 |
| | 0 | 4 | 5 | 4 | 5 | 2 |
| 83 | 0 | 4 | 5 | 3 | 5 | 2 |
| | 0 | 2 | 3 | 3 | 3 | 0 |
| 84 | 0 | 5 | 5 | 5 | 5 | 5 |
| | 0 | 5 | 5 | 4 | 5 | 3 |
| 85 | 0 | 5 | 5 | 5 | 5 | 5 |
| | 0 | 5 | 5 | 5 | 5 | 3 |
| 86 | 0 | 4 | 5 | 5 | 5 | 3 |
| | 0 | 3 | 5 | 4 | 5 | 2 |
| 87 | 0 | 5 | 5 | 5 | 5 | 3 |
| | 0 | 5 | 5 | 5 | 5 | 1 |
| 88 | 0 | 5 | 5 | 5 | 5 | 5 |
| | 0 | 5 | 5 | 5 | 5 | 5 |
| 89 | 0 | 5 | 5 | 5 | 5 | 5 |
| | 0 | 5 | 5 | 5 | 5 | 3 |
| 90 | 0 | 5 | 5 | 5 | 5 | 4 |
| | 0 | 5 | 5 | 5 | 5 | 2 |
| 91 | 0 | 5 | 5 | 4 | 5 | 3 |
| | 0 | 3 | 5 | 3 | 5 | 2 |
| 92 | 0 | 4 | 5 | 5 | 5 | 3 |
| | 0 | 2 | 4 | 4 | 5 | 1 |
| 93 | 0 | 4 | 5 | 5 | 5 | 4 |
| | 0 | 3 | 5 | 5 | 5 | 1 |
| 94 | 0 | 4 | 5 | 4 | 5 | 2 |
| | 0 | 3 | 4 | 2 | 3 | 0 |
| 95 | 0 | 3 | 5 | 4 | 5 | 2 |
| | 0 | 2 | 5 | 3 | 5 | 2 |
| 96 | 0 | 3 | 5 | 3 | 5 | 3 |
| | 0 | 2 | 5 | 3 | 5 | 1 |
| 97 | 0 | 5 | 5 | 5 | 5 | 5 |
| | 0 | 5 | 5 | 4 | 5 | 3 |
| 98 | 0 | 5 | 5 | 5 | 5 | 4 |
| | 0 | 4 | 5 | 5 | 5 | 2 |
| 99 | 0 | 5 | 5 | 5 | 5 | 5 |
| | 0 | 5 | 5 | 5 | 5 | 5 |
| 100 | 0 | 5 | 5 | 5 | 5 | 4 |
| | 0 | 5 | 5 | 4 | 5 | 2 |
| 101 | 0 | 5 | 5 | 5 | 5 | 2 |
| | 0 | 4 | 4 | 5 | 5 | 2 |

TABLE 2-continued

| | | | | | | |
|---|---|---|---|---|---|---|
| 102 | 0 | 5 | 5 | 5 | 5 | 3 |
| | 0 | 5 | 5 | 5 | 5 | 3 |
| 103 | 0 | 5 | 5 | 5 | 5 | 2 |
| | 0 | 3 | 5 | 5 | 5 | 1 |
| 104 | 0 | 5 | 5 | 5 | 5 | 3 |
| | 0 | 5 | 5 | 4 | 5 | 2 |
| 105 | 0 | 5 | 5 | 5 | 5 | 4 |
| | 0 | 4 | 5 | 4 | 4 | 2 |
| 106 | 0 | 5 | 5 | 5 | 5 | 2 |
| | 0 | 3 | 5 | 4 | 5 | 2 |
| 107 | 0 | 4 | 5 | 4 | 5 | 2 |
| | 0 | 2 | 3 | 2 | 3 | 0 |
| 108 | 0 | 5 | 5 | 5 | 5 | 3 |
| | 0 | 5 | 5 | 5 | 5 | 2 |
| 109 | 0 | 5 | 5 | 5 | 5 | 4 |
| | 0 | 5 | 5 | 5 | 5 | 2 |
| 110 | 0 | 5 | 4 | 3 | 5 | 2 |
| | 0 | 3 | 2 | 3 | 4 | 2 |
| 111 | 0 | 5 | 5 | 4 | 5 | 2 |
| | 0 | 5 | 5 | 3 | 5 | 1 |
| 112 | 0 | 5 | 5 | 5 | 5 | 5 |
| | 0 | 5 | 5 | 5 | 5 | 3 |
| 113 | 0 | 5 | 5 | 4 | 4 | 4 |
| | 0 | 4 | 5 | 2 | 3 | 2 |
| 114 | 0 | 5 | 5 | 4 | 5 | 2 |
| | 0 | 4 | 5 | 2 | 2 | 2 |
| 115 | 0 | 5 | 5 | 4 | 4 | 2 |
| | 0 | 3 | 5 | 2 | 2 | 2 |
| 116 | 0 | 5 | 5 | 3 | 5 | 3 |
| | 0 | 5 | 5 | 2 | 3 | 2 |
| 117 | 0 | 5 | 5 | 4 | 5 | 2 |
| | 0 | 5 | 5 | 2 | 5 | 2 |
| 118 | 0 | 5 | 5 | 3 | 5 | 2 |
| | 0 | 3 | 5 | 3 | 2 | 2 |
| 119 | 0 | 5 | 5 | 4 | 4 | 2 |
| | 0 | 3 | 5 | 1 | 2 | 1 |
| 120 | 0 | 5 | 5 | 4 | 4 | 3 |
| | 0 | 4 | 5 | 2 | 2 | 2 |
| 121 | 1 | 4 | 5 | 5 | 5 | 5 |
| | 0 | 3 | 5 | 4 | 5 | 4 |
| 122 | 0 | 5 | 5 | 5 | 5 | 3 |
| | 0 | 5 | 5 | 5 | 5 | 1 |
| 123 | 2 | 5 | 5 | 5 | 5 | — |
| | 1 | 5 | 5 | 4 | 4 | — |
| 126 | 0 | 5 | 5 | 5 | 5 | — |
| | 0 | 5 | 5 | 5 | 5 | — |
| 127 | 0 | 5 | 5 | 5 | 5 | — |
| | 0 | 5 | 5 | 5 | 5 | — |
| 128 | 0 | 5 | 5 | 5 | 5 | — |
| | 0 | 5 | 5 | 5 | 5 | — |
| 129 | 0 | 5 | 5 | 5 | 5 | — |
| | 0 | 5 | 5 | 5 | 5 | — |
| 130 | 0 | 5 | 5 | 5 | 5 | — |
| | 0 | 5 | 5 | 5 | 5 | — |
| 131 | 0 | 5 | 5 | 5 | 5 | — |
| | 0 | 5 | 5 | 4 | 4.5 | — |
| 132 | 0 | 5 | 5 | 5 | 5 | — |
| | 0 | 5 | 5 | 5 | 5 | — |
| 133 | 0 | 5 | 5 | 5 | 5 | — |
| | 0 | 5 | 5 | 4 | 5 | — |
| 134 | 0 | 5 | 5 | 5 | 5 | — |
| | 0 | 5 | 5 | 5 | 5 | — |
| 135 | 0 | 5 | 5 | 5 | 5 | — |
| | 0 | 5 | 5 | 5 | 5 | — |
| 136 | 0 | 5 | 5 | 5 | 5 | — |
| | 0 | 5 | 5 | 5 | 5 | — |
| 137 | 2 | 5 | 5 | 5 | 5 | — |
| | 0 | 5 | 5 | 5 | 5 | — |
| 138 | 0 | 5 | 5 | 5 | 5 | — |
| | 0 | 5 | 5 | 5 | 5 | — |
| 139 | 1 | 5 | 5 | 5 | 5 | — |
| | 0 | 5 | 5 | 5 | 5 | — |
| 140 | 0 | 5 | 5 | 5 | 5 | — |
| | 0 | 5 | 5 | 5 | 5 | — |
| 141 | 1 | 5 | 5 | 5 | 5 | — |
| | 0 | 4 | 5 | 3 | 4 | — |
| 142 | 0 | 5 | 5 | 5 | 5 | — |
| | 0 | 5 | 5 | 5 | 5 | — |
| 143 | 0 | 5 | 5 | 5 | 5 | — |
| | 0 | 5 | 5 | 3 | 5 | — |
| 146 | 0 | 5 | 5 | 5 | 5 | — |
| | 0 | 5 | 5 | 5 | 5 | — |

TABLE 2-continued

| Compound No. | Phytotoxicity against rice plant | barnyard-grass | broad leaved weeds | S. hotarui Ohwi. | C. difformis L. | C. serotinus Rottb. |
|---|---|---|---|---|---|---|
| 152 | 0 | 5 | 5 | 5 | 5 | — |
|  | 0 | 5 | 5 | 3 | 5 | — |
| 153 | 0 | 5 | 5 | 5 | 5 | — |
|  | 0 | 5 | 5 | 5 | 5 | — |
| 154 | 0 | 5 | 5 | 5 | 5 | — |
|  | 0 | 5 | 5 | 5 | 5 | — |
| 156 | 2 | 5 | 5 | 5 | 5 | — |
|  | 1 | 5 | 5 | 5 | 5 | — |
| 160 | 0 | 5 | 5 | 5 | 5 | — |
|  | 0 | 5 | 5 | 5 | 5 | — |
| 163 | 0 | 5 | 5 | 5 | 5 | — |
|  | 0 | 5 | 5 | 4 | 5 | — |
| 165 | 0 | 5 | 5 | 5 | 5 | — |
|  | 0 | 5 | 5 | 4 | 5 | — |
| 167 | 0 | 5 | 5 | 5 | 5 | — |
|  | 0 | 5 | 5 | 5 | 5 | — |
| 168 | 0 | 5 | 5 | 5 | 5 | — |
|  | 0 | 5 | 5 | 5 | 5 | — |
| 169 | 0 | 5 | 5 | 5 | 5 | — |
|  | 0 | 4 | 4 | 5 | 5 | — |
| 171 | 0 | 5 | 5 | 5 | 5 | — |
|  | 0 | 5 | 5 | 4 | 5 | — |
| 172 | 0 | 5 | 5 | 5 | 5 | — |
|  | 0 | 5 | 5 | 5 | 5 | — |
| 176 | 0 | 5 | 5 | 5 | 5 | — |
|  | 0 | 5 | 5 | 5 | 5 | — |
| 177 | 0 | 5 | 5 | 5 | 5 | — |
|  | 0 | 4 | 5 | 5 | 5 | — |
| 179 | 0 | 5 | 5 | 5 | 5 | — |
|  | 0 | 5 | 5 | 5 | 5 | — |
| 180 | 0 | 5 | 5 | 5 | 5 | — |
|  | 0 | 5 | 5 | 5 | 5 | — |
| 181 | 1 | 5 | 5 | 5 | 5 | 5 |
|  | 0 | 5 | 5 | 5 | 5 | 5 |
| 182 | 0 | 5 | 5 | 5 | 5 | 5 |
|  | 0 | 5 | 5 | 5 | 5 | 5 |
| 183 | 0 | 5 | 5 | 5 | 5 | 4 |
|  | 0 | 5 | 5 | 5 | 5 | 2 |
| 184 | 0 | 5 | 5 | 4 | 4 | 3 |
|  | 0 | 4 | 5 | 3 | 3 | 1 |
| 185 | 1 | 5 | 5 | 5 | 5 | 4 |
|  | 0 | 5 | 4 | 5 | 5 | 4 |
| 186 | 0 | 5 | 5 | 5 | 5 | 4 |
|  | 0 | 5 | 5 | 4 | 5 | 3 |
| 187 | 0 | 5 | 5 | 5 | 5 | 4 |
|  | 0 | 5 | 5 | 4 | 5 | 1 |
| 188 | 0 | 5 | 5 | 5 | 5 | 3 |
|  | 0 | 5 | 5 | 5 | 5 | 3 |
| 189 | 0 | 5 | 5 | 5 | 5 | 3 |
|  | 0 | 5 | 5 | 5 | 5 | 1 |
| 190 | 0 | 5 | 5 | 5 | 5 | 5 |
|  | 0 | 5 | 5 | 5 | 5 | 5 |
| 191 | 1 | 5 | 5 | 5 | 5 | 5 |
|  | 0 | 5 | 5 | 5 | 5 | 5 |
| 192 | 0 | 5 | 5 | 5 | 5 | 5 |
|  | 0 | 5 | 5 | 5 | 5 | 5 |
| 193 | 0 | 5 | 5 | 5 | 5 | 2 |
|  | 0 | 4 | 4 | 3 | 3 | 1 |
| 194 | 0 | 5 | 5 | 5 | 5 | 5 |
|  | 0 | 5 | 5 | 5 | 5 | 5 |
| 195 | 0 | 5 | 5 | 5 | 5 | 4 |
|  | 0 | 5 | 5 | 5 | 5 | 3 |
| 196 | 0 | 5 | 5 | 5 | 5 | 3 |
|  | 0 | 5 | 5 | 5 | 5 | 2 |
| 197 | 0 | 5 | 5 | 5 | 5 | 4 |
|  | 0 | 5 | 5 | 5 | 5 | 2 |
| 198 | 0 | 5 | 5 | 5 | 5 | 3 |
|  | 0 | 5 | 5 | 5 | 5 | 1 |
| 199 | 0 | 5 | 5 | 5 | 5 | 4 |
|  | 0 | 5 | 5 | 5 | 5 | 2 |
| 200 | 0 | 5 | 5 | 5 | 5 | 4 |
|  | 0 | 5 | 5 | 5 | 5 | 1 |
| 201 | 0 | 5 | 5 | 5 | 5 | 3 |
|  | 0 | 5 | 5 | 5 | 5 | 3 |
| 202 | 0 | 5 | 5 | 4 | 5 | 2 |
|  | 0 | 5 | 4 | 3 | 4 | 1 |

TABLE 2-continued

| | | | | | | |
|---|---|---|---|---|---|---|
| 203 | 0 | 5 | 5 | 5 | 5 | 5 |
| | 0 | 5 | 5 | 5 | 5 | 5 |
| 204 | 1 | 5 | 5 | 5 | 5 | 5 |
| | 0 | 5 | 5 | 5 | 5 | 4 |
| 205 | 0 | 5 | 5 | 5 | 5 | 3 |
| | 0 | 4 | 5 | 5 | 5 | 3 |
| 206 | 1 | 5 | 5 | 5 | 5 | 4 |
| | 0 | 5 | 5 | 5 | 5 | 4 |
| 207 | 0 | 5 | 4 | 5 | 5 | 5 |
| | 0 | 5 | 4 | 4 | 4 | 4 |
| 208 | 0 | 5 | 5 | 5 | 5 | 3 |
| | 0 | 3 | 5 | 4 | 4 | 1 |
| 209 | 1 | 5 | 5 | 5 | 5 | 5 |
| | 0 | 5 | 5 | 5 | 5 | 5 |
| 210 | 0 | 5 | 5 | 5 | 5 | 3 |
| | 0 | 5 | 5 | 5 | 5 | 1 |
| 211 | 1 | 5 | 5 | 5 | 5 | 5 |
| | 1 | 5 | 5 | 5 | 5 | 5 |
| 212 | 0 | 5 | 5 | 4 | 5 | 4 |
| | 0 | 5 | 5 | 4 | 5 | 4 |
| 213 | 0 | 5 | 5 | 5 | 5 | 5 |
| | 0 | 5 | 5 | 5 | 5 | 5 |
| 214 | 0 | 5 | 5 | 5 | 5 | 5 |
| | 0 | 5 | 5 | 5 | 5 | 4 |
| 215 | 0 | 5 | 4 | 5 | 5 | 4 |
| | 0 | 5 | 4 | 5 | 5 | 3 |
| 216 | 0 | 4 | 5 | 2 | 3 | 2 |
| | 0 | 3 | 5 | 1 | 1 | 1 |
| 217 | 0 | 5 | 5 | 5 | 5 | 5 |
| | 0 | 5 | 5 | 5 | 5 | 4 |
| 218 | 1 | 5 | 5 | 5 | 5 | 5 |
| | 0 | 4 | 5 | 4 | 5 | 4 |
| 219 | 0 | 5 | 4 | 4 | 4 | 3 |
| | 0 | 5 | 2 | 3 | 4 | 1 |
| 220 | 0 | 5 | 4 | 3 | 4 | 3 |
| | 0 | 4 | 3 | 1 | 3 | 1 |
| 221 | 0 | 5 | 5 | 5 | 5 | 4 |
| | 0 | 5 | 5 | 5 | 5 | 2 |
| 222 | 0 | 5 | 5 | 5 | 5 | 2 |
| | 0 | 5 | 5 | 4 | 5 | 1 |
| 223 | 0 | 5 | 5 | 5 | 5 | 3 |
| | 0 | 5 | 5 | 5 | 5 | 1 |
| 224 | 0 | 4 | 5 | 5 | 5 | 2 |
| | 0 | 4 | 4 | 4 | 5 | 1 |
| 225 | 0 | 5 | 5 | 5 | 5 | 4 |
| | 0 | 5 | 5 | 3 | 5 | 2 |
| 226 | 0 | 4 | 4 | 4 | 5 | 2 |
| | 0 | 3 | 4 | 3 | 5 | 1 |
| 227 | 1 | 5 | 5 | 5 | 5 | 5 |
| | 0 | 5 | 5 | 5 | 5 | 5 |
| 228 | 0 | 5 | 5 | 5 | 5 | 4 |
| | 0 | 5 | 5 | 5 | 5 | 3 |
| 229 | 0 | 5 | 5 | 5 | 5 | 5 |
| | 0 | 5 | 5 | 5 | 5 | 5 |
| 230 | 0 | 5 | 5 | 5 | 5 | 4 |
| | 0 | 5 | 5 | 4 | 5 | 4 |
| 231 | 0 | 5 | 5 | 5 | 5 | 4 |
| | 0 | 5 | 5 | 4 | 5 | 3 |
| 232 | 0 | 4 | 4 | 4 | 3 | 2 |
| | 0 | 2 | 3 | 3 | 3 | 1 |
| 233 | 0 | 5 | 5 | 5 | 5 | 4 |
| | 0 | 5 | 5 | 5 | 5 | 3 |
| 234 | 0 | 5 | 5 | 4 | 5 | 4 |
| | 0 | 5 | 5 | 4 | 5 | 4 |
| 235 | 0 | 3 | 4 | 4 | 4 | 3 |
| | 0 | 2 | 1 | 2 | 3 | 3 |
| 236 | 0 | 5 | 5 | 5 | 5 | 4 |
| | 0 | 5 | 5 | 5 | 5 | 4 |
| 237 | 0 | 5 | 4 | 5 | 5 | 3 |
| | 0 | 5 | 3 | 4 | 5 | 1 |
| 238 | 0 | 5 | 5 | 4 | 5 | 2 |
| | 0 | 5 | 5 | 3 | 5 | 1 |
| 239 | 0 | 5 | 5 | 4 | 5 | 4 |
| | 0 | 5 | 4 | 3 | 5 | 3 |
| 240 | 0 | 5 | 5 | 5 | 5 | 4 |
| | 0 | 5 | 5 | 4 | 5 | 4 |
| 241 | 0 | 5 | 5 | 4 | 5 | 4 |
| | 0 | 5 | 5 | 4 | 5 | 2 |
| 242 | 0 | 4 | 3 | 4 | 3 | 1 |
| | 0 | 3 | 3 | 2 | 1 | 1 |
| 243 | 0 | 5 | 5 | 4 | 5 | 4 |
| | 0 | 5 | 5 | 4 | 5 | 4 |

TABLE 2-continued

| | | | | | | |
|---|---|---|---|---|---|---|
| 244 | 0 | 5 | 5 | 5 | 5 | 5 |
| | 0 | 5 | 5 | 5 | 5 | 4 |
| 245 | 0 | 4 | 5 | 4 | 5 | 3 |
| | 0 | 4 | 5 | 3 | 4 | 3 |
| 246 | 0 | 5 | 5 | 5 | 5 | 5 |
| | 0 | 5 | 5 | 5 | 5 | 5 |
| 247 | 0 | 5 | 5 | 5 | 5 | 4 |
| | 0 | 5 | 5 | 5 | 5 | 2 |
| 248 | 0 | 5 | 5 | 4 | 5 | 4 |
| | 0 | 5 | 4 | 2 | 5 | 1 |
| 249 | 0 | 5 | 5 | 5 | 5 | 4 |
| | 0 | 5 | 5 | 5 | 5 | 3 |
| 250 | 0 | 5 | 5 | 4 | 5 | 3 |
| | 0 | 4 | 5 | 4 | 5 | 1 |
| 251 | 0 | 5 | 5 | 5 | 5 | 3 |
| | 0 | 5 | 5 | 5 | 5 | 2 |
| 252 | 0 | 5 | 5 | 5 | 5 | 4 |
| | 0 | 5 | 5 | 5 | 5 | 2 |
| 253 | 0 | 5 | 5 | 5 | 5 | 4 |
| | 0 | 5 | 5 | 5 | 5 | 2 |
| Napro-anilide* | 2 | 5 | 5 | 5 | 5 | — |
| | 1 | 4 | 5 | 5 | 5 | — |

*Effective ingredient, 2-(β-naphthoxy)-propioanilide.

EXPERIMENT 2

Soil treatment tests for upland weed control

Pots, each having an area of 1/5000 are, were packed with upland soil (diluvial soil) and then seeds of corn, of soybean, of wheat, of barnyard millet (*Echinochloa utilis Ohwi.*), of large crabgrass (*Digitaria adscendens Henr.*), of clover, of common purslane (*Portulaca oleracea L.*), of barnyardgrass (*Echinochloa crusgalli Beauv.*), or of redroot pigweed (*Amaranthus retroflexus L.*) were sowed therein. After covering with soil, a predetermined amount of a dilute solution of each wettable powder, which had been prepared in the same manner as in Herbicidal composition 2 above, was uniformly spread by using a pressure sprayer.

Three weeks after the treatment, the herbicidal effects of each test compound were investigated.

The results are shown in Table 3 wherein the same rating system as defined in Experiment 1 is applied.

The data on the upper and lower lines in each column of Table 3 show the results which were obtained by carrying out the experiments at concentrations of an active ingredient of 50 g/are and 25 g/are, respectively.

TABLE 3

| Compound No. | Phytotoxicity against crops | | | Herbicidal effects | | | | | | |
|---|---|---|---|---|---|---|---|---|---|---|
| | corn | soybean | wheat | barnyard millet | large crabgrass | clover | common purslane | common lambsquatens | barnyard-grass | redroot pigweed |
| 1 | 0 | 0 | — | 3 | 5 | 4 | 5 | 5 | — | — |
| | 0 | 0 | — | 2 | 3 | 2 | 5 | 4 | — | — |
| 16 | 1 | 0 | — | 5 | 5 | 5 | 5 | 5 | — | — |
| | 0 | 0 | — | 3 | 5 | 5 | 5 | 5 | — | — |
| 30 | 1 | 1 | — | 4 | 5 | 5 | 5 | 5 | — | — |
| | 0 | 0 | — | 3 | 5 | 5 | 5 | 5 | — | — |
| 32 | 0 | 0 | — | 4 | 5 | 5 | 5 | 5 | — | — |
| | 0 | 0 | — | 2 | 4 | 5 | 5 | 3 | — | — |
| 48 | 0 | 0 | — | 3 | 5 | 5 | 5 | 4 | — | — |
| | 0 | 0 | — | 2 | 5 | 5 | 5 | 3 | — | — |
| 49 | 1 | 1 | — | 5 | 5 | 5 | 5 | 5 | — | — |
| | 0 | 0 | — | 5 | 5 | 5 | 5 | 5 | — | — |
| 50 | 1 | 1 | — | 5 | 5 | 5 | 5 | 5 | — | — |
| | 0 | 0 | — | 5 | 5 | 5 | 5 | 5 | — | — |
| 55 | 1 | 0 | — | 5 | 5 | 5 | 5 | 5 | — | — |
| | 0 | 0 | — | 5 | 5 | 5 | 5 | 5 | — | — |
| 56 | 1 | 0 | — | 5 | 5 | 5 | 5 | 5 | — | — |
| | 0 | 0 | — | 5 | 5 | 5 | 5 | 5 | — | — |
| 71 | 0 | 0 | — | 4 | 5 | 4 | 5 | 5 | — | — |
| | 0 | 0 | — | 3 | 5 | 3 | 5 | 4 | — | — |
| 85 | 0 | 0 | — | 4 | 5 | 5 | 5 | 5 | — | — |
| | 0 | 0 | — | 2 | 5 | 5 | 5 | 3 | — | — |
| 88 | 0 | 0 | — | 4 | 4 | 4 | 5 | 4 | — | — |
| | 0 | 0 | — | 2 | 3 | 2 | 5 | 2 | — | — |
| 89 | 0 | 0 | — | 4 | 5 | 5 | 5 | 5 | — | — |
| | 0 | 0 | — | 2 | 4 | 5 | 5 | 3 | — | — |
| 99 | 0 | 0 | — | 4 | 5 | 5 | 5 | 4 | — | — |
| | 0 | 0 | — | 3 | 5 | 5 | 5 | 4 | — | — |
| 103 | 0 | 0 | — | 3 | 4 | 4 | 5 | 4 | — | — |
| | 0 | 0 | — | 2 | 2 | 4 | 5 | 2 | — | — |
| 181 | — | 0 | 0 | — | 5 | — | — | 5 | 5 | 5 |
| | — | 0 | 0 | — | 5 | — | — | 5 | 5 | 5 |
| 188 | — | 0 | 0 | — | 4 | — | — | 4 | 4 | 5 |
| | — | 0 | 0 | — | 2 | — | — | 4 | 3 | 3 |
| 190 | — | 0 | 0 | — | 5 | — | — | 3 | 4 | 5 |

TABLE 3-continued

| Compound No. | Phytotoxicity against crops | | | Herbicidal effects | | | | | | |
|---|---|---|---|---|---|---|---|---|---|---|
| | corn | soybean | wheat | barnyard millet | large crabgrass | clover | common purslane | common lambsquatens | barnyard-grass | redroot pigweed |
| | — | 0 | 0 | — | 3 | — | — | 1 | 3 | 3 |
| 191 | — | 0 | 0 | — | 5 | — | — | 5 | 5 | 5 |
| | — | 0 | 0 | — | 4 | — | — | 5 | 5 | 5 |
| 209 | — | 0 | 0 | — | 5 | — | — | 5 | 5 | 5 |
| | — | 0 | 0 | — | 5 | — | — | 5 | 5 | 5 |
| 213 | — | 0 | 0 | — | 5 | — | — | 5 | 4 | 5 |
| | — | 0 | 0 | — | 5 | — | — | 5 | 5 | 5 |
| 226 | — | 0 | 0 | — | 5 | — | — | 5 | 5 | 5 |
| | — | 0 | 0 | — | 5 | — | — | 5 | 5 | 5 |
| 227 | — | 0 | 0 | — | 5 | — | — | 5 | 5 | 5 |
| | — | 0 | 0 | — | 5 | — | — | 5 | 5 | 5 |
| 236 | — | 0 | 0 | — | 5 | — | — | 4 | 4 | 5 |
| | — | 0 | 0 | — | 5 | — | — | 3 | 3 | 3 |

From the experimental results shown above, it is understood that the herbicidal composition of this invention is highly harmless to various crops and shows excellent herbicidal effects against various kinds of weeds, and it is recognized that the herbicidal composition of this invention is an extremely excellent selective herbicidal composition.

EXPERIMENT 3

Foliar spread test for upland weed control

Pots, each having an area of 1/15500 are, were packed with upland soil (diluvial soil) and then planted with wheat, large crabgrass and redroot pigweed.

When each plant grew up to 2~3 leaf stage, a 0.50% by weight (wt %) or 0.25 wt % solution of each wettable powder, which had been prepared in the same manner as in Herbicidal composition 2 above, was spread for treatment by using a pressure sprayer.

Two weeks after the treatment, the herbicidal effects of each test compound were investigated.

The results are shown in Table 4 wherein the same rating system as defined in Experiment 1 is applied.

The data on the upper and lower lines in each column of Table 4 show the results which were obtained by carrying out the experiments at concentrations of an active ingredient of 0.50 wt % and 0.25 wt %, respectively.

TABLE 4

| Compound No. | Phytotoxicity against crops wheat | Herbicidal effects | |
|---|---|---|---|
| | | large crabgrass | redroot pigweed |
| 129 | 2 | 4 | 5 |
| | 0 | 3 | 3 |
| 138 | 2 | 5 | 5 |
| | 0 | 5 | 4 |
| 139 | 1 | 5 | 5 |
| | 0 | 5 | 5 |
| 154 | 1 | 5 | 5 |
| | 0 | 5 | 3 |
| 158 | 0 | 5 | 5 |
| | 0 | 5 | 5 |
| 165 | 0 | 5 | 4 |
| | 0 | 5 | 4 |
| 168 | 0 | 5 | 5 |
| | 0 | 5 | 5 |
| 176 | 0 | 5 | 5 |
| | 0 | 5 | 5 |

From the experimental results shown above, it is understood that the herbicidal composition of this invention is highly harmless to crops and shows excellent herbicidal effects against various kinds of weeds, and it is recognized that the herbicidal composition of this invention is an extremely excellent selective herbicidal composition.

EXPERIMENT 4

A paddy field soild of sandy loam was filled into a 1/5000 are Wagner pot, followed by watering and puddling. Two days after puddling, a 1000 ppm diluted solution of each wettable powder prepared similarly as in Herbicidal composition 16 was added dropwise to predetermined dosages of the ingredients for treatment of the soil. On the next day after the treatment, young paddy rice seedlings at the two-leaf stage (species: Nipponbare) were transplanted, two hills per one pot, with two seedlings for one hill. Each pot, after the treatment repeated twice for each treatment, was taken care of night and day in a water bath of 35° C. On the 25th day after the treatment, the extent of chemical damage on the paddy rice was examined according to the following standards:

—: no damage (normal growth)
±: the first leaf sheath slightly whitened
+: about half of the first leaf sheath whitened
++: whole of the first leaf sheath whitened
+++: whole of the first leaf sheath whitened, and the first leaf blade slightly whitened
X: paddy rice as a whole whitened.

The results are shown in Table 5.

TABLE 5

| Chemicals tested (g/are) | | Chemical damage on paddy rice |
|---|---|---|
| Benzylamide derivative of phenoxyalkanoic acid | Dymrone | |
| Compound No. 30: 50 | 25 | — |
| | 0 | ++ |
| Compound No. 49: 50 | 25 | — |
| | 0 | + |
| Compound No. 51: 50 | 25 | — |
| | 0 | ++ |
| Compound No. 55: 50 | 25 | —~± |
| | 0 | ++ |
| Compound No. 58: 50 | 25 | — |
| | 0 | ± |
| Compound No. 60: 50 | 25 | ± |
| | 0 | +++ |
| Compound No. 74: 50 | 25 | ± |
| | 0 | +++ |
| Compound No. 99: 50 | 25 | —~± |
| | 0 | ++ |
| Compound No. 105: 50 | 25 | —~± |
| | 0 | ++ |
| Compound No. 181: 50 | 25 | + |
| | 0 | +++ |
| Compound No. 209: 50 | 25 | — |
| | 0 | ++ |
| Compound No. 226: 50 | 25 | ± |

TABLE 5-continued

| Chemicals tested (g/are) | | Chemical damage on paddy rice |
|---|---|---|
| Benzylamide derivative of phenoxyalkanoic acid | Dymrone | |
| | 0 | ++ |
| Compound No. 251: 50 | 25 | − |
| | 0 | + |
| Compound No. 252: 50 | 25 | −~± |
| | 0 | ++ |
| Compound No. 253: 50 | 25 | − |
| | 0 | ++ |

EXPERIMENT 5

A paddy field of sandy loam was filled into a 1/6000 are pot, followed by watering, puddling and submerging to a water depth of 2 cm.

Next day, a 1000 ppm diluted solution of each wettable powder prepared similarly as in Herbicidal composition 16 was added dropwise for treatment of the soil. On the next day after the treatment, paddy rice seeds (species: Nipponbare) just onset of germination to the extent of pigeon-breast were seeded, 20 grains for each pot. Each pot was subjected to the treatment which was repeated twice per one treatment, and taken care of in a green house. On the 25th day after the treatment, chemical damage on paddy rice was examined according to the same standards as in Experiment 4.

The results are shown in Table 6.

TABLE 6

| Chemicals tested (g/are) | | Chemical damage on paddy rice |
|---|---|---|
| Benzylamide derivative of phenoxyalkanoic acid | Dymrone | |
| Compound No. 49: 20 | 15 | − |
| | 0 | ++ |
| Compound No. 49: 40 | 15 | − |
| | 0 | +++ |
| Compound No. 58: 20 | 15 | − |
| | 0 | ++ |
| Compound No. 58: 40 | 15 | − |
| | 0 | +++ |
| Compound No. 60: 20 | 15 | − |
| | 0 | ± |
| Compound No. 60: 40 | 15 | − |
| | 0 | + |
| Compound No. 251: 20 | 15 | − |
| | 0 | ++ |
| Compound No. 251: 40 | 15 | − |
| | 0 | +++ |
| Compound No. 252: 20 | 15 | − |
| | 0 | ++ |
| Compound No. 252: 40 | 15 | − |
| | 0 | +++ |
| Compound No. 253: 20 | 15 | − |
| | 0 | ± |
| Compound No. 253: 40 | 15 | − |
| | 0 | + |

EXPERIMENT 6

A 1/5000 are Wagner pot was filled with sandy loam, and water was added thereinto to carry out puddling. Then, seeds of barnyard grass, Scipus hotarui Ohwi, Monochoria (Monochoria vaginalis Pres.) and annual broad leaf weed were seeded, followed by submerging to a water depth of 3 cm. Next day after seeding, a 1000 ppm diluted solution of each wettable powder prepared similarly as in Herbicidal composition 16 was added dropwise to dosages of 50 g of a benzylamide derivative of phenoxyalkanoic acid and 25 g of dymrone per are.

On 25th day after the treatment, the herbicidal effect was evaluted according to the same rating system as defined in Experiment 1.

The results are shown in Table 7.

TABLE 7

| | Herbicidal effect | | |
|---|---|---|---|
| Benzylamide derivative of phenoxyalkanoic acid | Barnyard grass | Scripus hotarui Ohwi | Monochoria and annual broad leaf weed |
| Compound No. 30 | 5 | 5 | 5 |
| Compound No. 49 | 5 | 5 | 5 |
| Compound No. 51 | 5 | 5 | 5 |
| Compound No. 55 | 5 | 5 | 5 |
| Compound No. 58 | 5 | 5 | 5 |
| Compound No. 60 | 5 | 5 | 5 |
| Compound No. 74 | 5 | 5 | 5 |
| Compound No. 99 | 5 | 5 | 5 |
| Compound No. 105 | 5 | 5 | 5 |
| Compound No. 181 | 5 | 5 | 5 |
| Compound No. 209 | 5 | 5 | 5 |
| Compound No. 226 | 5 | 5 | 5 |
| Compound No. 251 | 5 | 5 | 5 |
| Compound No. 252 | 5 | 5 | 5 |
| Compound No. 253 | 5 | 5 | 5 |

EXPERIMENT 7

A 1/5000 are Wagner pot was filled with a paddy field soil of sandy loam, and water was added thereinto to carry out puddling. Then, seeds of barnyard grass, Scipus hotarui Ohwi, Monochoria (Monochoria vaginalis Pres.) and annual broad leaf weed were seeded, followed by submerging to a water depth of 3 cm. On the third day after seeding, a 1000 ppm diluted solution of each wettable powder prepared similarly as in Herbicidal composition 16 was added dropwise to treat each paddy field.

On the next day after the treatment, young paddy rice seedlings at the two-leaf stage (species: Nipponbare) were transplanted, two hills per one pot, with two seedlings for one hill. Each pot, after the treatment repeated twice for each treatment, was taken care of in a green house. On the 25th day after the treatment, the extent of chemical damage on the paddy rice was examined according to the same standards as in Experiment 4 and the herbicidal effect according to the same standards as in Experiment 1.

The results are shown in Table 8.

TABLE 8

| Chemicals tested (g/are) | | | | Chemical damage on paddy field | Herbicidal effect | | |
|---|---|---|---|---|---|---|---|
| Benzylamide derivative of phenoxyalkanoic acid | Dymrone | Pyrazolate or Naproanilide* | | | Barnyard grass | Scripus hotarui Ohwi | Monochoria and annual broad leaf weed |
| Compound No. 55: 20 | 0 | Pyrazolate | 0 | + | 5 | 5 | 5 |
| | 10 | | 0 | − | 5 | 5 | 5 |
| | 20 | | 0 | − | 5 | 5 | 5 |
| | 10 | | 20 | − | 5 | 5 | 5 |

TABLE 8-continued

| Chemicals tested (g/are) | | | Herbicidal effect | | | |
|---|---|---|---|---|---|---|
| Benzylamide derivative of phenoxyalkanoic acid | Dymrone | Pyrazolate or Naproanilide* | Chemical damage on paddy field | Barnyard grass | *Scripus hotarui* Ohwi | Monochoria and annual broad leaf weed |
| | 20 | | 20 | — | 5 | 5 | 5 |
| | 10 | Napro- | 20 | — | 5 | 5 | 5 |
| | 20 | anilide | 20 | — | 5 | 5 | 5 |
| Compound No. 209: 20 | 0 | Pyrazo- | 0 | ± | 5 | 5 | 5 |
| | 10 | late | 0 | — | 5 | 5 | 5 |
| | 20 | | 0 | — | 5 | 5 | 5 |
| | 10 | | 20 | — | 5 | 5 | 5 |
| | 20 | | 20 | — | 5 | 5 | 5 |
| | 10 | Napro- | 20 | — | 5 | 5 | 5 |
| | 20 | anilide | 20 | — | 5 | 5 | 5 |

*Pyrazolate: 4-(2,4-dichlorobenzoyl)-1,3-dimethylpyrazol-5-yl-p-toluenesulfonate.
Naproanilide: α-(β-naphthoxy)propionanilide

EXPERIMENT 8

Soil treatment tests for paddy field weed

Pots, each having an area of 1/9000 are, were packed with paddy soil (diluvial soil) and planted with uniformly mixed seeds of barnyardgrass (*Echinochloa crusgalli*), of broad leaved weeds (*Rotla indica Koekne, Lindernia Pyxidaria L., Monochoria vaginalis*), of *Scripus hotarui* Ohwi. and of *Cyperus difformis L.* upon the surface layer, and rice plant seedlings at 1.8~3 leaf stage were also transplanted. Then, the pots were filled with water to a depth of 2~3 cm.

Then, 3 days later, i.e., at the initial stage of generation of each weed, a predetermined amount of dilute solution of a wettable powder of each test compound and comparative test compound, which had been prepared in the same manner as in Herbicidal composition 2 above, was uniformly spread to the surface of filled water.

Four weeks after the treatment, their herbicidal effects of each test compound and comparative compound were investigated.

The test results are shown in Table 9, 10 and 11 wherein the herbicidal effects are evaluated according to the rating system as defined in Experiment 1.

The data on the upper and lower lines in each column of Table 9, 10 and 11 are the results which were obtained by carrying out the experiments at concentrations of an active ingredient of 62.5 g/10 are and 31.25 g/10 are, respectively.

TABLE 9

| Compound No. | Chemical structure | Phytotoxicity against rice plant | Herbicidal effect | | | |
|---|---|---|---|---|---|---|
| | | | barnyard grass | broad leaved weeds | *Scripus hotarui* Ohwi. | *Cyperus difformis* L. |
| Comparative sample 1 | Cl—(3,4-diCl-phenyl)—OCHCONHCH₂—(phenyl), with CH₂OCH₃ branch (mp. 103–105° C.) | 0<br>0 | 1<br>0 | 3<br>2 | 0<br>0 | 4<br>0 |
| 99 | Cl—(3,4-diCl-phenyl)—OCHCONHCH₂—(phenyl), with C₂H₅ branch | 0<br>0 | 5<br>5 | 5<br>5 | 5<br>5 | 5<br>5 |
| 112 | Cl—(3,4-diCl-phenyl)—OCHCONHCH₂—(phenyl), with C₃H₇—n branch | 0<br>0 | 5<br>5 | 5<br>5 | 5<br>4 | 5<br>5 |
| Comparative sample 2 | Cl—(3-Cl-4-CH₃-phenyl)—OCHCONHCH₂—(phenyl), with CH₂OCH₃ branch (mp. 91–92° C.) | 0<br>0 | 1<br>0 | 2<br>0 | 1<br>0 | 2<br>0 |

TABLE 9-continued

| Compound No. | Chemical structure | Phyto-toxicity against rice plant | Herbicidal effect | | | |
|---|---|---|---|---|---|---|
| | | | barnyard grass | broad leaved weeds | *Scripus hotarui* Ohwi. | *Cyperus difformis* L. |
| 49 | Cl-[phenyl with CH₃]-OCH(C₂H₅)CONHCH₂-[phenyl] | 0<br>0 | 5<br>5 | 5<br>5 | 5<br>4 | 5<br>5 |
| 54 | Cl-[phenyl with CH₃]-OCH(C₃H₇-n)CONHCH₂-[phenyl] | 0<br>0 | 5<br>5 | 5<br>4 | 4<br>3 | 5<br>4 |
| Comparative sample 3 | Cl-[phenyl with CH₃, CH₃]-OCH₂CONHCH₂-[phenyl] (mp. 124–126° C.) | 0<br>0 | 0<br>0 | 0<br>0 | 0<br>0 | 0<br>0 |
| 55 | Cl-[phenyl with CH₃, CH₃]-OCH(C₂H₅)CONHCH₂-[phenyl] | 0<br>0 | 5<br>5 | 5<br>5 | 5<br>5 | 5<br>5 |
| Comparative sample 4 | Cl-[phenyl with CH₃]-OCH₂CONHCH₂-[phenyl] (mp. 85–86° C.) | 0<br>0 | 1<br>0 | 1<br>0 | 1<br>0 | 2<br>1 |
| Comparative sample 5 | Cl-[phenyl with CF₃]-OCH(CH₃)CONHCH₂-[phenyl] (mp. 68–70° C.) | 0<br>0 | 2<br>0 | 2<br>0 | 1<br>0 | 4<br>1 |
| 248 | Cl-[phenyl with CF₃]-OCH(C₃H₇-n)CONHCH₂-[phenyl] | 0<br>0 | 5<br>4 | 4<br>4 | 2<br>2 | 5<br>5 |

TABLE 10

| Compound No. | Chemical structure | Phyto-toxicity against rice plant | Herbicidal effect ||||
|---|---|---|---|---|---|---|
| | | | barnyard grass | broad leaved weeds | *Scripus hotarui* Ohwi. | *Cyperus difformis* L. |
| Comparative sample 6 | 3-Cl-C$_6$H$_4$-OCH(C$_2$H$_5$)CONHCH$_2$CH=CH$_2$ (mp. 48–50° C.) | 0<br>0 | 0<br>0 | 2<br>0 | 0<br>0 | 0<br>0 |
| Comparative sample 7 | 3-Cl-C$_6$H$_4$-OCH(C$_2$H$_5$)CONHCH$_2$C≡CH (n$_D^{26}$ = 1.5337) | 0<br>0 | 1<br>0 | 3<br>1 | 1<br>0 | 0<br>0 |
| 67 | 3-Cl-C$_6$H$_4$-OCH(C$_2$H$_5$)CONHCH$_2$-C$_6$H$_5$ | 0<br>0 | 4<br>4 | 5<br>5 | 5<br>5 | 5<br>5 |
| Comparative sample 8 | 3,4-Cl$_2$-C$_6$H$_3$-OCH(C$_2$H$_5$)CONHCH$_2$CH=CH$_2$ (mp. 64–66° C.) | 0<br>0 | 1<br>0 | 0<br>0 | 0<br>0 | 0<br>0 |
| Comparative sample 9 | 3,4-Cl$_2$-C$_6$H$_3$-OCH(C$_2$H$_5$)CONHCH$_2$C≡CH (mp. 78–80° C.) | 0<br>0 | 0<br>0 | 2<br>0 | 0<br>0 | 1<br>0 |
| 99 | 3,4-Cl$_2$-C$_6$H$_3$-OCH(C$_2$H$_5$)CONHCH$_2$-C$_6$H$_5$ | 0<br>0 | 5<br>5 | 5<br>5 | 5<br>5 | 5<br>5 |
| Comparative sample 10 | 3,5-Cl$_2$-C$_6$H$_3$-OCH(C$_2$H$_5$)CONHCH$_2$CH=CH$_2$ (mp. 92–93° C.) | 0<br>0 | 4<br>2 | 1<br>0 | 1<br>0 | 1<br>0 |
| Comparative sample 11 | 3,5-Cl$_2$-C$_6$H$_3$-OCH(C$_2$H$_5$)CONHCH$_2$C≡CH (mp. 99–101° C.) | 0<br>0 | 4<br>2 | 0<br>0 | 1<br>0 | 1<br>0 |

TABLE 10-continued

| Compound No. | Chemical structure | Phyto-toxicity against rice plant | Herbicidal effect | | | |
|---|---|---|---|---|---|---|
| | | | barnyard grass | broad leaved weeds | Scripus hotarui Ohwi. | Cyperus difformis L. |
| 113 | Cl-C6H3(Cl)-OCH(C2H5)CONHCH2-C6H5 | 0<br>0 | 4<br>4 | 5<br>4 | 2<br>2 | 4<br>3 |
| Comparative sample 12 | CF3-C6H4-OCH(C2H5)CONHCH2CH=CH2<br>(n_D^{24} = 1.4766) | 0<br>0 | 1<br>0 | 2<br>0 | 0<br>0 | 0<br>0 |
| Comparative sample 13 | CF3-C6H4-OCH(C2H5)CONHCH2C≡CH<br>(n_D^{14} = 1.4840) | 0<br>0 | 0<br>0 | 0<br>0 | 0<br>0 | 0<br>0 |
| 209 | CF3-C6H4-OCH(C2H5)CONHCH2-C6H4(Cl) | 0<br>0 | 5<br>5 | 5<br>5 | 5<br>5 | 5<br>5 |

TABLE 11

| Compound No. | Chemical structure | Phyto-toxicity against rice plant | Herbicidal effect | | | |
|---|---|---|---|---|---|---|
| | | | barnyard grass | broad leaved weeds | Scripus hotarui Ohwi. | Cyperus difformis L. |
| Comparative sample 14 | 2-Pyridyl-OCH(C2H5)CONHCH2-C6H5<br>(mp. 93–97° C.) | 0<br>0 | 0<br>0 | 0<br>0 | 0<br>0 | 0<br>0 |
| Comparative sample 15 | 3-Pyridyl-OCH(C2H5)CONHCH2-C6H5<br>(mp. 75–78° C.) | 0<br>0 | 0<br>0 | 1<br>0 | 0<br>0 | 3<br>1 |
| 1 | C6H5-OCH(C2H5)CONHCH2-C6H5 | 0<br>0 | 4<br>3 | 5<br>4 | 3<br>2 | 5<br>4 |

From the experimental results shown in Table 9, it is understood that the herbicidal composition of this invention wherein $R^1$ in the general formula (I) is an ethyl group or n-propyl group is highly harmless to various crops and shows excellent herbicidal effect against various kinds of weeds, and it is recognized that the herbicidal composition of this invention is an extremely excellent seletive herbicidal composition.

On the other hand, the herbicidal composition of the comparative sample in which $R^1$ is a hydrogen atom, methyl group or methoxymethyl group is extremely inferior in the herbicidal effect as compared with the herbicidal composition of this invention.

Further, from the experimental results shown in Table 10, it is understood that the herbicidal composition of this invention wherein Z in the general formula (I) is a substituted or unsubstituted phenyl group, naphthyl group, thienyl group, pyridyl group or furyl group shows excellent herbicidal activity and other characteristics as mentioned above, whereas the comparative sample in which Z of the present invention is replaced with a vinyl group or acetylene group is extremely inferior in herbicidal effect etc.

Moreover, from the experimental results shown in Table 11, it is understood that the herbicidal composition of this invention wherein the phenoxyalkylamido derivative having phenoxy group represented by the formula

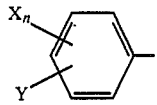

is employed shows excellent herbicidal effect and other characteristics as mentioned above, whereas the comparative sample in which the phenoxy group of the present invention is replaced with a pyridyloxy group does not show excellent herbicidal effect and the like.

We claim:

1. A herbicidal composition which comprises, as an active ingredient, a phenoxyalkylamide derivative represented by the formula

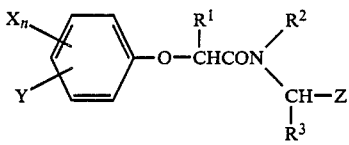

wherein
X: a lower-alkyl group, a lower-alkoxy group, a halogen atom, a cyano group, a nitro group or a propionyl group;
n: an integer of 0 to 3, provided that, when n is an integer of 2 or 3, Xs may be the same or different;
Y: a hydrogen atom, a lower-alkyl group, a lower-alkoxy group, a trifluoromethyl group or a nitro group;
Z: a phenyl group, a substituted phenyl group represented by the following formula

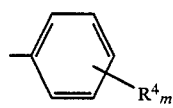

(in which $R^4$ represents a lower-alkyl group, a lower-alkoxy group, a nitro group or a halogen atom; and m is an integer of 1 or 2, provided that, when m is 2, $R^4$s may be the same or different), a naphthyl group, a thienyl group, a pyridyl group or a furyl group;
$R^1$: an ethyl group or an n-propyl group;
$R^2$: a hydrogen atom, a lower-alkyl group, a lower alkenyl group, a lower-alkynyl group or a lower-alkoxy group; and
$R^3$: a hydrogen atom or a lower-alkyl group, and an agriculturally acceptable amount of a carrier.

2. A herbicidal composition as defined in claim 1, wherein the phenoxyalkylamide derivative is represented by the formula

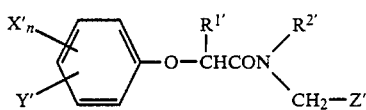

wherein
X': a methyl group or a chlorine atom;
n: an integer of 0 to 3, provided that, when n is an integer of 2 or 3, X's may be the same or different;
Y': a hydrogen atom or a trifluoromethyl group;
Z': a phenyl group, a 2-methylphenyl group, a 2-chlorophenyl group, a thienyl group, a 2-pyridyl group or a 3-pyridyl group;
$R^{1'}$: an ethyl group; and
$R^{2'}$: a hydrogen atom or a methyl group.

3. A herbicidal composition according to claim 1, wherein the active ingredient is selected from the group consisting of the compounds shown below:
N-Benzyl-2-(4-chloro-3-methylphenoxy)-butyramide
N-Benzyl-N-methyl-2-(4-chloro-3-methylphenoxy)-butyramide
N-Benzyl-2-(4-chloro-3,5-dimethylphenoxy)-butyramide
N-Benzyl-N-methyl-2-(4-chloro-3,5-dimethylphenoxy)-butyramide
N-(2-Methylbenzyl)-2-(4-chloro-3,5-dimethylphenoxy)-butyramide
N-Benzyl-2-(3,4-dichlorophenoxy)-butyramide
N-Benzyl-2-(3,4-dichlorophenoxy)-valeramide
N-(2-Pyridylmethyl)-2-(3,5-dimethylphenoxy)-butyramide
N-Thienylmethyl-2-(4-chloro-3-methylphenoxy)-butyramide
N-Thienylmethyl-2-(4-chloro-3,5-dimethylphenoxy)-butyramide
N-(2-Pyridylmethyl)-2-(4-chloro-3,5-dimethylphenoxy)-butyramide
N-(3-Pyridylmethyl)-2-(4-chloro-3,5-dimethylphenoxy)-butyramide
N-Benzyl-2-(3-trifluoromethylphenoxy)-butyramide
N-(2-Chlorobenzyl)-2-(3-trifluoromethylphenoxy)-butyramide
N-Thienylmethyl-2-(3-trifluoromethylphenoxy)-butyramide
N-Benzyl-2-(4-chloro-3-trifluoromethylphenoxy)-butyramide
N-Benzyl-N-methyl-2-(4-chloro-3-trifluoromethylphenoxy)-butyramide
N-(3-Pyridylmethyl)-2-(4-chloro-3-trifluoromethylphenoxy)-butyramide
N-(2-Chlorobenzyl)-2-(4-chloro-3-methylphenoxy)-butyramide
N-(2-Chlorobenzyl)-2-(4-chloro-3,5-dimethylphenoxy)-butyramide
N-(2-Methoxybenzyl)-2-(4-chloro-3-methylphenoxy)-butyramide.

4. A method for controlling weeds which comprise applying to such weeds an effective amount of a phenoxyalkylamide compound having the formula

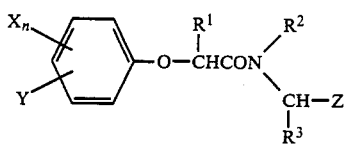

wherein
- X: a lower-alkyl group, a lower-alkoxy group, a halogen atom, a cyano group, a nitro group or a propionyl group;
- n: an integer of 0 to 3, provided that, when n is an integer of 2 or 3, Xs may be the same or different;
- Y: a hydrogen atom, a lower-alkyl group, a lower-alkoxy group, a trifluoromethyl group or a nitro group;
- Z: a phenyl group, a substituted phenyl group represented by the following formula

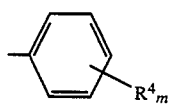

(in which $R^4$ represents a lower-alkyl group, a lower-alkoxy group, a nitro group or a halogen atom; and m is an integer of 1 or 2, provided that, when m is 2, $R^4$s may be the same or different), a naphthyl group, a thienyl group, a pyridyl group or a furyl group;
- $R^1$: an ethyl group or an n-propyl group;
- $R^2$: a hydrogen atom, a lower-alkyl group, a lower-alkenyl group, a lower-alkynyl group or a lower-alkoxy group; and
- $R^3$: a hydrogen atom or a lower-alkyl group, and an agriculturally acceptable amount of a carrier.

5. A method for controlling weeds as defined in claim 4, wherein the phenoxyalkylamide derivative is represented by the formula

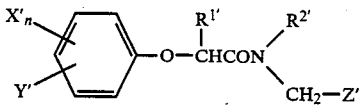

wherein

- $X'$: a methyl group or a chlorine atom;
- n: an integer of 0 to 3, provided that, when n is an integer of 2 or 3, X's may be the same or different;
- $Y'$: a hydrogen atom or a trifluoromethyl group;
- $Z'$: a phenyl group, a 2-methylphenyl group, a 2-chlorophenyl group, a thienyl group, a 2-pyridyl group or a 3-pyridyl group;
- $R^{1'}$: an ethyl group; and
- $R^{2'}$: a hydrogen atom or a methyl group.

6. A method for controlling weeds as defined in claim 4, wherein the phenoxyalkylamide derivative is selected from the group consisting of the compounds shown below:
N-Benzyl-2-(4-chloro-3-trifluoromethylphenoxy)-butyramide
N-Benzyl-N-methyl-2-(4-chloro-3-trifluoromethylphenoxy)-butyramide
N-(3-Pyridylmethyl)-2-(4-chloro-3-trifluoromethylphenoxy)-butyramide
N-(2-Chlorobenzyl)-2-(4-chloro-3-methylphenoxy)-butyramide
N-(2-Chlorobenzyl)-2-(4-chloro-3,5-dimethylphenoxy)-butyramide
N-(2-Methoxybenzyl)-2-(4-chloro-3-methylphenoxy)-butyramide.

7. A method for controlling weeds according to claim 4, wherein the amount of the phenoxyalkylamide derivative is in the range between 0.5 g/are and 100 g/are.

8. A method for controlling weeds as defined in claim 4, wherein the phenoxyalkylamide derivative is a benzylamide derivative of a phenoxyalkanoic acid represented by the formula:

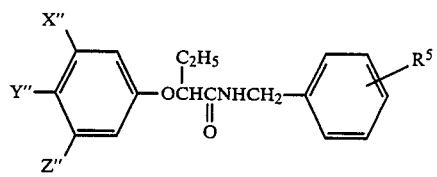

wherein
- $X''$: a methyl group or a hydrogen atom;
- $Y''$: a halogen atom or a hydrogen atom;
- $Z''$: a methyl group, a halogen atom or a trifluoromethyl group; and
- $R^5$: a methyl group, a methoxy group, a halogen atom or a hydrogen atom.

* * * * *